US008034773B2

(12) United States Patent
Eggink et al.

(10) Patent No.: US 8,034,773 B2
(45) Date of Patent: Oct. 11, 2011

(54) IMMUNOSTIMULATORY COMPOSITIONS AND USES THEREOF

(75) Inventors: Laura L. Eggink, Scottsdale, AZ (US); Valerie Jacobs, West Lebanon, NH (US); Kenneth Hoober, Phoenix, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 546 days.

(21) Appl. No.: 10/588,627

(22) PCT Filed: Feb. 4, 2005

(86) PCT No.: PCT/US2005/003766
§ 371 (c)(1),
(2), (4) Date: Oct. 15, 2008

(87) PCT Pub. No.: WO2005/087793
PCT Pub. Date: Sep. 22, 2005

(65) Prior Publication Data
US 2009/0041793 A1     Feb. 12, 2009

Related U.S. Application Data

(60) Provisional application No. 60/542,198, filed on Feb. 5, 2004, provisional application No. 60/633,825, filed on Dec. 7, 2004.

(51) Int. Cl.
*A61K 38/10* (2006.01)
*A61K 38/16* (2006.01)
*C07K 14/00* (2006.01)
*C07K 7/00* (2006.01)
*C07K 7/08* (2006.01)
*C07K 4/00* (2006.01)

(52) U.S. Cl. ......... 514/14; 514/21.5; 530/324; 530/325; 530/326; 530/327; 435/69.1

(58) Field of Classification Search ........................ None
See application file for complete search history.

(56) References Cited

U.S. PATENT DOCUMENTS

| | | | |
|---|---|---|---|
| 5,641,747 | A | 6/1997 | Popoff et al. |
| 5,677,276 | A | 10/1997 | Dickerson et al. |
| 5,753,481 | A | 5/1998 | Niwa et al. |
| 5,910,310 | A | 6/1999 | Heinen et al. |
| 5,919,998 | A | 7/1999 | Bandurski et al. |
| 6,159,937 | A | 12/2000 | Larsen et al. |
| 6,193,981 | B1 | 2/2001 | Goldstein |
| 6,498,020 | B1 | 12/2002 | Walker et al. |
| 6,551,795 | B1 * | 4/2003 | Rubenfield et al. .......... 435/69.1 |
| 7,105,481 | B2 | 9/2006 | Uutela et al. |
| 2003/0073637 | A1 | 4/2003 | Uutela et al. |
| 2004/0031072 | A1 | 2/2004 | La Rosa et al. |
| 2004/0123343 | A1 | 6/2004 | La Rosa et al. |
| 2004/0248192 | A1 | 12/2004 | Marchalonis et al. |
| 2005/0063937 | A1 | 3/2005 | Li et al. |
| 2006/0024668 | A1 | 2/2006 | Hock |
| 2006/0078535 | A1 | 4/2006 | Livant |
| 2006/0148093 | A1 | 7/2006 | Gygi et al. |
| 2006/0160730 | A1 | 7/2006 | Cuttitta et al. |
| 2006/0189538 | A1 | 8/2006 | Secombes et al. |
| 2006/0269519 | A1 | 11/2006 | Chen et al. |
| 2006/0287234 | A1 | 12/2006 | Breen et al. |
| 2007/0003542 | A1 | 1/2007 | Zimmerman et al. |
| 2007/0021342 | A1 | 1/2007 | Breen et al. |
| 2007/0149475 | A1 | 6/2007 | Murray et al. |
| 2007/0154448 | A1 | 7/2007 | Reid et al. |
| 2008/0102076 | A1 | 5/2008 | Eggink et al. |
| 2009/0041793 | A1 | 2/2009 | Eggink et al. |

FOREIGN PATENT DOCUMENTS

| | | |
|---|---|---|
| CA | 2290722 | 6/2001 |
| WO | WO-96/40903 A1 | 12/1996 |
| WO | WO-00/31130 A1 | 6/2000 |
| WO | WO-02/058589 A2 | 8/2002 |
| WO | 03/091275 | 11/2003 |
| WO | 04/011650 | 2/2004 |
| WO | 05/087793 | 9/2005 |
| WO | 06/063028 | 6/2006 |
| WO | 2006/105021 | 10/2006 |

OTHER PUBLICATIONS

European Search Report for European patent application No. 07869233.2 dated May 11, 2010.
GlaxoSmithKline, (2005a) Study of Chemokine Coreceptor 5 (CCR5) Antagonist GW873140 in R5-Tropic Treatment-Experienced HIV Infected Subjects, ClinicalTrials.gov (Sep. 13, 2005) Identifier: NCT00197145S, (Terminated in 2005).
GlaxoSmithKline, (2005b) "GlaxoSmithKline Halts Trials of Experimental CCR5 Inhibitor Aplaviroc in Treatnnentnaïve HIV Patients Due to Concerns about Liver Toxicity," Statement of HIV Patient Community: Information from GlaxoSmithKline on Changes to Studies Investigational CCR5 Entry Inhibitor Aplaviroc (GW873140) (Sep. 15, 2005), pp. 1-2.
International Search Report for WO/2006/063028 dated Nov. 16, 2006 (6 sheets).
International Search Report for WO/2005/087793 dated Apr. 5, 2006 (6 sheets).
PCT/US2007/087413 International Search Report dated Jul. 29, 2008.
PCT/US2007/087425 International Search Report dated Aug. 5, 2008.
Supplementary European Search Report for European application No. 07871699.0 dated May 17, 2010 (8 sheets).
Written Opinion of the International Searching Authority for WO/2005/087793 dated Apr. 5, 2006 (7 sheets).
Written Opinion of the International Searching Authority for WO/2006/063028 dated Nov. 16, 2006 (9 sheets).
Written Opinion of the International Searching Authority for WO/2008/076815 dated Jul. 29, 2008 (6 sheets).
Written Opinion of the International Searching Authority for WO/2008/076824 dated Aug. 5, 2008 (6 sheets).

(Continued)

*Primary Examiner* — Christine J Saoud
(74) *Attorney, Agent, or Firm* — Banner & Witcoff, Ltd.

(57) ABSTRACT

The present invention provides novel immuno-stimulatory polypeptides, and methods for their use and identification.

20 Claims, 11 Drawing Sheets

OTHER PUBLICATIONS

Chargelegue et al., "A Peptide Mimic of a Protective Epitope of Respiratory Syncytial Virus Selected from a Combinatorial Library Induces Virus-Neutralizing Antibodies and Reduces Viral Load in Vivo", Journal of Virology, 72 (3):2040-2046 (Mar. 1998).

Chersi et al., "Specifications of rabbit antisera to multiple antigen (MAP) peptides", ournal of Biosciences, 50 (9-10):735-738 (Sep. 1, 1995) Abstract Only.

Ciesielski et al., "Cellular antitumor immune response to a branched lysine multiple antigenic peptide containing epitopes of a common tumor-specific antigen in a rat giloma model", Cancer Immunol Immunother, 54:107-119 (2005).

Eggink et al., "A biologically active peptide mimetic of N-acetylgalactosamine/galactose", BMC Research Notes, 2:23 (2009).

G.Fätkenheuer et al., "Efficacy of Short-Term Monotherapy with Maraviroc, a New CRC5 Antagonist, in Patients Infected with HIV 1," Natire Med (2005), vol. 11, pp. 1170-1172.

J. Cohen, "Hope on New AIDS Drugs, but Breast-Feeding Strategy Backfires," Science (2007), vol. 315, p. 1357.

J. Stover et al., "The Global Impact of Scaling up HIV/AIDS Prevention Programs in Low-and Middle-Income Countries," Science (2006) vol. 311, pp. 1474-1476.

Manki et al., "Vaccination with Multiple Antigen Peptide as Rejection Antigen Peptide in Murine Leukemia", Cancer Research, 58:1960-1964 (May 1, 1998).

Nicolaus, "Symbiotic Approach to Drug Design", Decision Making in Drug Research, pp. 173-186 (Jan. 1, 1983).

Olszewska et al., "Protection against Measles Virus-Induced Encephalitis by Anti-mimotope Antibodies: The Rose of Antibody Affinity" Virology, 272(1):98-105 (Jun. 20, 2000).

P.W. Latham, "Therapeutic Peptides Revisited," Nature Biotech (1999), vol. 17, pp. 755-757.

Sarig et al., "Telomeric and Tetraplex DNA Binding Properties of qTBP42: A Homologue of the CArG Box Binding Protein CBF-A"; Biochemical and Biophysical Research Communications 1997, vol. 237, No. 3, pp. 617-623.

* cited by examiner

```
DNA: 5'-GTG CAG GCT ACT CAG TCT AAT CAG CAT ACG CCG CGG GGT GGA GGT TCG

AA:      V   Q   A   T   Q   S   N   Q   H   T   P   R   G   G   G   S
    [                  Mimetic Sequence                  ] [    Spacer    ]
```

Figure 1

5-((((2-iodoacetyl)amino)ethyl)amino)naphthalene-1-sulfonic acid (1,5-IAEDANS)

Molecular Formula: $C_{14}H_{15}IN_2O_4S$

Molecular Weight: 434.25

CAS Number/Name: 36930-63-9 / 1-Naphthalenesulfonic acid, 5-((2-((iodoacetyl)amino)ethyl)amino)-

Amino acid sequence of polypeptide encoded in sequence in capital letters in A.

Met
LCADYSENTFTEYKKKLAERLKAKLPDATPQATQSNQHTPRGGGSELAKL
VNKHSDFASNCCSINSPPLYCDSEIDAELKNILHHHHHH

Figure 6

Leu Cys Ala Asp Tyr Ser Glu Asn Thr Phe Thr Glu Tyr Lys Lys Lys
1         5            10            15

Leu Ala Glu Arg Leu Lys Ala Lys Leu Pro Asp Ala Thr Pro Gln Ala
       20           25           30

Thr Gln Ser Asn Gln His Thr Pro Arg Gly Gly Gly Ser Glu Leu Ala
       35           40           45

Lys Leu Val Asn Lys His Ser Asp Phe Ala Ser Asn Cys Cys Ser Ile
    50           55           60

Asn Ser Pro Pro Leu Tyr Cys Asp Ser Glu Ile Asp Ala Glu Leu Lys
65           70           75           80

Asn Ile Leu

Figure 10

Met Leu Cys Ala Asp Tyr Ser Glu Asn Thr Phe Thr Glu Tyr Lys Lys
1           5               10              15

Lys Leu Ala Glu Arg Leu Lys Ala Lys Leu Pro Asp Ala Thr Pro Gln
        20              25              30

Ala Thr Gln Ser Asn Gln His Thr Pro Arg Gly Gly Gly Ser Glu Leu
        35              40              45

Ala Lys Leu Val Asn Lys His Ser Asp Phe Ala Ser Asn Cys Cys Ser
        50              55              60

Ile Asn Ser Pro Pro Leu Tyr Cys Asp Ser Glu Ile Asp Ala Glu Leu
        65              70              75              80

Lys Asn Ile Leu His His His His His His
        85              90

Figure 11

SEQUENCE LISTING

```
<160> NUMBER OF SEQ ID NOS: 45

<210> SEQ ID NO 1
<211> LENGTH: 12
<212> TYPE: PRT
<213> ORGANISM: Artificial sequence
<220> FEATURE:
<223> OTHER INFORMATION: Synthetic peptide

<400> SEQUENCE: 1

Ala Gln Ala Leu Gly Leu Ser Ala Ile Ser Pro Arg
1               5                   10

<210> SEQ ID NO 2
<211> LENGTH: 12
<212> TYPE: PRT
<213> ORGANISM: Artificial sequence
<220> FEATURE:
<223> OTHER INFORMATION: Synthetic peptide

<400> SEQUENCE: 2

Cys Thr Asp Glu Ala Leu Tyr Thr Arg Arg Gln Cys
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

Val Gln Ala Thr Gln Ser Asn Gln His Thr Pro Arg
1               5                   10

<210> SEQ ID NO 4
<211> LENGTH: 12
<212> TYPE: PRT
<213> ORGANISM: Artificial sequence
<220> FEATURE:
<223> OTHER INFORMATION: Synthetic peptide

<400> SEQUENCE: 4

Glu Gln Ala Thr Pro Arg Asn His His Ser Pro Pro
1               5                   10

<210> SEQ ID NO 5
<211> LENGTH: 12
<212> TYPE: PRT
<213> ORGANISM: Artificial sequence
<220> FEATURE:
<223> OTHER INFORMATION: Synthetic peptide

<400> SEQUENCE: 5

Val Gln Ala Thr Pro Arg Leu Gln His Thr Pro Arg
1               5                   10

<210> SEQ ID NO 6
<211> LENGTH: 12
<212> TYPE: PRT
<213> ORGANISM: Artificial sequence
<220> FEATURE:
<223> OTHER INFORMATION: Synthetic peptide

<400> SEQUENCE: 6

Ala Gln Gly Pro Pro Ser Lys Gln His Ser Pro Pro
```

```
<210> SEQ ID NO 7
<211> LENGTH: 12
<212> TYPE: PRT
<213> ORGANISM: Artificial sequence
<220> FEATURE:
<223> OTHER INFORMATION: Synthetic peptide

<400> SEQUENCE: 7

Leu Pro Thr Thr Ile Asn Ile Ser Asn Arg Gly Ser
1               5                   10

<210> SEQ ID NO 8
<211> LENGTH: 11
<212> TYPE: PRT
<213> ORGANISM: Artificial sequence
<220> FEATURE:
<223> OTHER INFORMATION: Synthetic peptide

<400> SEQUENCE: 8

Val Pro Phe Arg Gly Tyr Ser Pro Pro Gln Gly
1               5                   10

<210> SEQ ID NO 9
<211> LENGTH: 12
<212> TYPE: PRT
<213> ORGANISM: Artificial sequence
<220> FEATURE:
<223> OTHER INFORMATION: Synthetic peptide

<400> SEQUENCE: 9

Val Gln Ala Ile Gln Ser Asn Gln Leu Thr Pro Arg
1               5                   10

<210> SEQ ID NO 10
<211> LENGTH: 12
<212> TYPE: PRT
<213> ORGANISM: Artificial sequence
<220> FEATURE:
<223> OTHER INFORMATION: Synthetic peptide

<400> SEQUENCE: 10

Val Gln Ala Thr Thr Val Gln Ile Gln His Ala Pro
1               5                   10

<210> SEQ ID NO 11
<211> LENGTH: 12
<212> TYPE: PRT
<213> ORGANISM: Artificial sequence
<220> FEATURE:
<223> OTHER INFORMATION: Synthetic peptide

<400> SEQUENCE: 11

Cys Arg Ala Ser Ile Asn Ile Thr Asn Arg Gly Ser
1               5                   10

<210> SEQ ID NO 12
<211> LENGTH: 12
<212> TYPE: PRT
<213> ORGANISM: Artificial sequence
<220> FEATURE:
<223> OTHER INFORMATION: Synthetic peptide

<400> SEQUENCE: 12

Leu Pro Ser Thr Ile Asn Ile Thr Asn Arg Gly Ser
1               5                   10
```

<210> SEQ ID NO 13
<211> LENGTH: 12
<212> TYPE: PRT
<213> ORGANISM: Artificial sequence
<220> FEATURE:
<223> OTHER INFORMATION: Synthetic peptide

<400> SEQUENCE: 13

Gln Ser Thr Thr Ile Asn Ile Ile Arg Ser Gly Ser
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic peptide

<400> SEQUENCE: 14

Glu Glu Ala Ile Ser Leu Ile Ser Ile Arg Arg Arg
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthetic peptide

<400> SEQUENCE: 15

Val Gln Ala Gly Gln Ser Asn Ala His Thr Ala Gly
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetic peptide

<400> SEQUENCE: 16

Thr Thr Asp Glu Pro Phe Val Tyr Arg Arg Gln Pro
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide

<400> SEQUENCE: 17

Val Gln Ala Arg Gln Ser Asn Gln His Thr Pro Arg
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetic peptide

<400> SEQUENCE: 18

Val Gln Ala Asn Gln Cys Gln Ser Ala Tyr Ala Arg
1               5                   10

<210> SEQ ID NO 19

```
<211> LENGTH: 12
<212> TYPE: PRT
<213> ORGANISM: Artificial sequence
<220> FEATURE:
<223> OTHER INFORMATION: Synthetic peptide

<400> SEQUENCE: 19

Val Arg Leu Leu Gln Tyr Ala His Arg Gly Arg Gly
1               5                   10

<210> SEQ ID NO 20
<211> LENGTH: 12
<212> TYPE: PRT
<213> ORGANISM: Artificial sequence
<220> FEATURE:
<223> OTHER INFORMATION: Synthetic peptide

<400> SEQUENCE: 20

Val Gln Asn Tyr Gln Ser Asn Gln His Thr Pro Arg
1               5                   10

<210> SEQ ID NO 21
<211> LENGTH: 11
<212> TYPE: PRT
<213> ORGANISM: Artificial sequence
<220> FEATURE:
<223> OTHER INFORMATION: Synthetic peptide

<400> SEQUENCE: 21

Phe Val Ser Thr Thr Met Lys Leu Ser Asp Gly
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic peptide

<400> SEQUENCE: 22

Phe Asn Ser Tyr Asp Thr Glu Ala Phe Gly Gly Ser
1               5                   10

<210> SEQ ID NO 23
<211> LENGTH: 10
<212> TYPE: PRT
<213> ORGANISM: Artificial sequence
<220> FEATURE:
<223> OTHER INFORMATION: Synthetic peptide

<400> SEQUENCE: 23

Ala Glu Thr Val Glu Ser Cys Leu Ala Lys
1               5                   10

<210> SEQ ID NO 24
<211> LENGTH: 1801
<212> TYPE: DNA
<213> ORGANISM: Homo sapiens

<400> SEQUENCE: 24
tttaataata attctgtgtt gcttctgaga ttaataattg attaattcat agtcaggaat      60
ctttgtaaaa aggaaaccaa ttactttggg ctaccacttt tacatggtca cctacaggag    120
agaggaggtg ctgcaagact ctctggtaga aaaatgaaga gggtcctggt actactgctt    180
gctgtggcat ttggacatgc tttagagaga ggccgggatt atgaaaagaa taaagtctgc    240
aaggaattct cccatctggg aaaggaggac ttcacatctc tgtcactagt cctgtacagt    300
```

```
agaaaatttc ccagtggcac gtttgaacag gtcagccaac ttgtgaagga agttgtctcc    360
ttgaccgaag cctgctgtgc ggaaggggct gaccctgact gctatgacac caggacctca    420
gcactgtctg ccaagtcctg tgaaagtaat tctccattcc ccgttcaccc aggcactgct    480
gagtgctgca ccaaagaggg cctggaacga agctctgca tggctgctct gaaacaccag     540
ccacaggaat tccctaccta cgtggaaccc acaaatgatg aaatctgtga ggcgttcagg    600
aaagatccaa aggaatatgc taatcaattt atgtgggaat attccactaa ttacggacaa    660
gctcctctgt cacttttagt cagttacacc aagagttatc tttctatggt agggtcctgc    720
tgtacctctg caagcccaac tgtatgcttt ttgaaagaga gactccagct taaacattta    780
tcacttctca ccactctgtc aaatagagtc tgctcacaat atgctgctta tggggagaag    840
aaatcaaggc tcagcaatct cataaagtta gcccaaaaag tgcctactgc tgatctggag    900
gatgttttgc cactagctga agatattact aacatcctct ccaaatgctg tgagtctgcc    960
tctgaagatt gcatggccaa agagctgcct gaacacacag taaaactctg tgacaattta   1020
tccacaaaga attctaagtt tgaagactgt tgtcaagaaa aaacagccat ggacgttttt   1080
gtgtgcactt acttcatgcc agctgcccaa ctcccccgagc ttccagatgt agagttgccc   1140
acaaacaaag atgtgtgtga tccaggaaac accaaagtca tggataagta catttgaa     1200
ctaagcagaa ggactcatct tccggaagta ttcctcagta aggtacttga gccaacccta   1260
aaaagccttg gtgaatgctg tgatgttgaa gactcaacta cctgttttaa tgctaagggc   1320
cctctactaa agaaggaact atcttctttc attgacaagg gacaagaact atgtgcagat   1380
tattcagaaa atacatttac tgagtacaag aaaaaactgg cagagcgact aaaagcaaaa   1440
tgcctgatg ccacacccac ggaactggca aagctggtta acaagcactc agactttgcc    1500
tccaactgct gttccataaa ctcacctcct ctttactgtg attcagagat tgatgctgaa   1560
ttgaagaata tcctgtagtc ctgaagcatg tttattaact ttgaccagag ttggagccac   1620
ccagggggaat gatctctgat gacctaaccT aagcaaaacc actgagcttc tgggaagaca   1680
actaggatac tttctacttt ttctagctac aatatcttca tacaatgaca agtatgatga   1740
tttgctatca aaataaattg aaatataatg caaaccataa aaaaaaaaaa aaaaaaaaa    1800
a                                                                    1801
```

<210> SEQ ID NO 25
<211> LENGTH: 474
<212> TYPE: PRT
<213> ORGANISM: Homo sapiens

<400> SEQUENCE: 25

```
Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
```

```
            100                 105                 110
Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr
                405                 410                 415

Glu Tyr Lys Lys Lys Leu Ala Glu Arg Leu Lys Ala Lys Leu Pro Asp
            420                 425                 430

Ala Thr Pro Thr Glu Leu Ala Lys Leu Val Asn Lys His Ser Asp Phe
        435                 440                 445

Ala Ser Asn Cys Cys Ser Ile Asn Ser Pro Pro Leu Tyr Cys Asp Ser
450                 455                 460

Glu Ile Asp Ala Glu Leu Lys Asn Ile Leu
465                 470

<210> SEQ ID NO 26
<211> LENGTH: 207
<212> TYPE: DNA
<213> ORGANISM: Homo sapiens
<220> FEATURE:
<221> NAME/KEY: CDS
<222> LOCATION: (1)..(207)
```

```
<400> SEQUENCE: 26 cta tgt gca gat tat tca gaa aat aca ttt act gag tac aag aaa aaa    48
Leu Cys Ala Asp Tyr Ser Glu Asn Thr Phe Thr Glu Tyr Lys Lys Lys
1               5                   10                  15 ctg gca gag cga cta aaa gca aaa ttg cct gat gcc aca ccc acg gaa    96
Leu Ala Glu Arg Leu Lys Ala Lys Leu Pro Asp Ala Thr Pro Thr Glu
            20                  25                  30 ctg gca aag ctg gtt aac aag cac tca gac ttt gcc tcc aac tgc tgt   144
Leu Ala Lys Leu Val Asn Lys His Ser Asp Phe Ala Ser Asn Cys Cys
        35                  40                  45 tcc ata aac tca cct cct ctt tac tgt gat tca gag att gat gct gaa   192
Ser Ile Asn Ser Pro Pro Leu Tyr Cys Asp Ser Glu Ile Asp Ala Glu
    50                  55                  60 ttg aag aat atc ctg                                                207
Leu Lys Asn Ile Leu
65

<210> SEQ ID NO 27
<211> LENGTH: 69
<212> TYPE: PRT
<213> ORGANISM: Homo sapiens

<400> SEQUENCE: 27

Leu Cys Ala Asp Tyr Ser Glu Asn Thr Phe Thr Glu Tyr Lys Lys Lys
1               5                   10                  15

Leu Ala Glu Arg Leu Lys Ala Lys Leu Pro Asp Ala Thr Pro Thr Glu
            20                  25                  30

Leu Ala Lys Leu Val Asn Lys His Ser Asp Phe Ala Ser Asn Cys Cys
        35                  40                  45

Ser Ile Asn Ser Pro Pro Leu Tyr Cys Asp Ser Glu Ile Asp Ala Glu
    50                  55                  60

Leu Lys Asn Ile Leu
65

<210> SEQ ID NO 28
<211> LENGTH: 249
<212> TYPE: DNA
<213> ORGANISM: Artificial sequence
<220> FEATURE:
<223> OTHER INFORMATION: Synthetic oligonucleotide
<220> FEATURE:
<221> NAME/KEY: CDS
<222> LOCATION: (1)..(249)

<400> SEQUENCE: 28 cta tgt gca gat tat tca gaa aat aca ttt act gag tac aag aaa aaa    48
Leu Cys Ala Asp Tyr Ser Glu Asn Thr Phe Thr Glu Tyr Lys Lys Lys
1               5                   10                  15 ctg gca gag cga cta aaa gca aaa ttg cct gat gcc aca ccc caa gct    96
Leu Ala Glu Arg Leu Lys Ala Lys Leu Pro Asp Ala Thr Pro Gln Ala
            20                  25                  30 aca caa tca aat caa cat aca cca cgt ggt ggt ggt tca gaa ctg gca   144
Thr Gln Ser Asn Gln His Thr Pro Arg Gly Gly Gly Ser Glu Leu Ala
        35                  40                  45 aag ctg gtt aac aag cac tca gac ttt gcc tcc aac tgc tgt tcc ata   192
Lys Leu Val Asn Lys His Ser Asp Phe Ala Ser Asn Cys Cys Ser Ile
    50                  55                  60 aac tca cct cct ctt tac tgt gat tca gag att gat gct gaa ttg aag   240
Asn Ser Pro Pro Leu Tyr Cys Asp Ser Glu Ile Asp Ala Glu Leu Lys
65                  70                  75                  80 aat atc ctg                                                        249
Asn Ile Leu
```

<210> SEQ ID NO 29
<211> LENGTH: 83
<212> TYPE: PRT
<213> ORGANISM: Artificial sequence
<220> FEATURE:
<223> OTHER INFORMATION: Synthetic Construct

<400> SEQUENCE: 29

Leu Cys Ala Asp Tyr Ser Glu Asn Thr Phe Thr Glu Tyr Lys Lys Lys
1               5                   10                  15

Leu Ala Glu Arg Leu Lys Ala Lys Leu Pro Asp Ala Thr Pro Gln Ala
            20                  25                  30

Thr Gln Ser Asn Gln His Thr Pro Arg Gly Gly Gly Ser Glu Leu Ala
        35                  40                  45

Lys Leu Val Asn Lys His Ser Asp Phe Ala Ser Asn Cys Cys Ser Ile
    50                  55                  60

Asn Ser Pro Pro Leu Tyr Cys Asp Ser Glu Ile Asp Ala Glu Leu Lys
65                  70                  75                  80

Asn Ile Leu

<210> SEQ ID NO 30
<211> LENGTH: 1031
<212> TYPE: DNA
<213> ORGANISM: Artificial sequence
<220> FEATURE:
<223> OTHER INFORMATION: Synthetic oligonucleotide
<220> FEATURE:
<221> NAME/KEY: CDS
<222> LOCATION: (214)..(486)

<400> SEQUENCE: 30
aaagatttta aaataaaact tttttaatct tttatttatt ttttcttttt tatggcaatg      60
cgtactccag aagaacttag taatcttatt aaagatttaa ttgaacaata cactccagaa     120
gtgaaaatgg tagatttcgg tatcgttttc caagtaggtg acggtattgc tcgtatttat     180
ggtttagaaa aagcaatgtc aggtgaatta ctt atg tta tgt gct gat tat tca     234
                                    Met Leu Cys Ala Asp Tyr Ser
                                    1               5 gaa aat aca ttt aca gaa tat aaa aaa aaa tta gct gaa cgt tta aaa     282
Glu Asn Thr Phe Thr Glu Tyr Lys Lys Lys Leu Ala Glu Arg Leu Lys
        10                  15                  20 gct aaa tta cca gat gct aca cca caa gct aca caa tca aat caa cat     330
Ala Lys Leu Pro Asp Ala Thr Pro Gln Ala Thr Gln Ser Asn Gln His
    25                  30                  35 aca cca cgt ggt ggt ggt tca gaa tta gct aaa tta gtt aat aaa cat     378
Thr Pro Arg Gly Gly Gly Ser Glu Leu Ala Lys Leu Val Asn Lys His
40                  45                  50                  55 tca gat ttt gct tca aat tgt tgt tca att aat tca cca cca tta tat     426
Ser Asp Phe Ala Ser Asn Cys Cys Ser Ile Asn Ser Pro Pro Leu Tyr
                60                  65                  70 tgt gat tca gaa att gat gct gaa tta aaa aat att tta cat cat cat     474
Cys Asp Ser Glu Ile Asp Ala Glu Leu Lys Asn Ile Leu His His His
            75                  80                  85 cat cat cat taa ttccaagcat tatctaaaat actctgcagg catgcaagct           526
His His His
        90 agcttgtact caagctcgta acgaaggtcg tgaccttgct cgtgaaggtg cgacgtaat     586 tcgttcagct tgtaaatggt ctccagaact tgctgctgca tgtgaagttt ggaaagaaat     646 taaattcgaa tttgatacta ttgacaaact ttaattttta tttttcatga tgtttatgtg     706

```
aatagcataa acatcgtttt tattttatg gtgtttaggt taaataccta aacatcattt    766 tacatttta aaattaagtt ctaaagttat cttttgttta aatttgcctg tctttataaa    826
ttacgatgtg ccagaaaaat aaaatcttag cttttatta tagaatttat ctttatgtat    886 tatatttat aagttataat aaaagaaata gtaacatact aaagcggatg tagcgcgttt    946
atcttaacgg aagtctagag gcatcgaatt cctgcagccc ggggatcca ctagttctag    1006 agcggccgcc accgcggtgg agctc                                         1031

<210> SEQ ID NO 31
<211> LENGTH: 90
<212> TYPE: PRT
<213> ORGANISM: Artificial sequence
<220> FEATURE:
<223> OTHER INFORMATION: Synthetic Construct

<400> SEQUENCE: 31

Met Leu Cys Ala Asp Tyr Ser Glu Asn Thr Phe Thr Glu Tyr Lys Lys
1               5                   10                  15

Lys Leu Ala Glu Arg Leu Lys Ala Lys Leu Pro Asp Ala Thr Pro Gln
            20                  25                  30

Ala Thr Gln Ser Asn Gln His Thr Pro Arg Gly Gly Gly Ser Glu Leu
        35                  40                  45

Ala Lys Leu Val Asn Lys His Ser Asp Phe Ala Ser Asn Cys Cys Ser
    50                  55                  60

Ile Asn Ser Pro Pro Leu Tyr Cys Asp Ser Glu Ile Asp Ala Glu Leu
65                  70                  75                  80

Lys Asn Ile Leu His His His His His His
            85                  90

<210> SEQ ID NO 32
<211> LENGTH: 18
<212> TYPE: PRT
<213> ORGANISM: Artificial sequence
<220> FEATURE:
<223> OTHER INFORMATION: Synthetic peptide

<400> SEQUENCE: 32

Val Gln Ala Thr Gln Ser Asn Gln His Thr Pro Arg Gly Gly Gly Ser
1               5                   10                  15

Lys Trp

<210> SEQ ID NO 33

<400> SEQUENCE: 33

000

<210> SEQ ID NO 34
<211> LENGTH: 4
<212> TYPE: PRT
<213> ORGANISM: Artificial sequence
<220> FEATURE:
<223> OTHER INFORMATION: Synthetic peptide

<400> SEQUENCE: 34

Gly Gly Gly Ser
1

<210> SEQ ID NO 35

<400> SEQUENCE: 35
```

000

```
<210> SEQ ID NO 36
<211> LENGTH: 11
<212> TYPE: PRT
<213> ORGANISM: Artificial sequence
<220> FEATURE:
<223> OTHER INFORMATION: Synthetic peptide

<400> SEQUENCE: 36

Gln Ala Thr Gln Ser Asn Gln His Thr Pro Arg
1               5                   10

<210> SEQ ID NO 37
<211> LENGTH: 15
<212> TYPE: PRT
<213> ORGANISM: Artificial sequence
<220> FEATURE:
<223> OTHER INFORMATION: Synthetic peptide

<400> SEQUENCE: 37

Gln Ala Thr Gln Ser Asn Gln His Thr Pro Arg Gly Gly Gly Ser
1               5                   10                  15

<210> SEQ ID NO 38
<211> LENGTH: 16
<212> TYPE: PRT
<213> ORGANISM: Artificial sequence
<220> FEATURE:
<223> OTHER INFORMATION: Synthetic peptide

<400> SEQUENCE: 38

Val Gln Ala Thr Gln Ser Asn Gln His Thr Pro Arg Gly Gly Gly Ser
1               5                   10                  15

<210> SEQ ID NO 39
<211> LENGTH: 12
<212> TYPE: PRT
<213> ORGANISM: Artificial sequence
<220> FEATURE:
<223> OTHER INFORMATION: Synthetic peptide

<400> SEQUENCE: 39

Gln Ala Thr Gln Ser Asn Gln His Thr Pro Arg Lys
1               5                   10

<210> SEQ ID NO 40
<211> LENGTH: 13
<212> TYPE: PRT
<213> ORGANISM: Artificial sequence
<220> FEATURE:
<223> OTHER INFORMATION: Synthetic peptide

<400> SEQUENCE: 40

Gln Ala Thr Gln Ser Asn Gln His Thr Pro Arg Lys Trp
1               5                   10

<210> SEQ ID NO 41
<211> LENGTH: 16
<212> TYPE: PRT
<213> ORGANISM: Artificial sequence
<220> FEATURE:
<223> OTHER INFORMATION: Synthetic peptide

<400> SEQUENCE: 41

Gln Ala Thr Gln Ser Asn Gln His Thr Pro Arg Gly Gly Gly Ser Lys
1               5                   10                  15
```

```
<210> SEQ ID NO 42
<211> LENGTH: 17
<212> TYPE: PRT
<213> ORGANISM: Artificial sequence
<220> FEATURE:
<223> OTHER INFORMATION: Synthetic peptide

<400> SEQUENCE: 42

Gln Ala Thr Gln Ser Asn Gln His Thr Pro Arg Gly Gly Gly Ser Lys
1               5                   10                  15

Trp

<210> SEQ ID NO 43
<211> LENGTH: 13
<212> TYPE: PRT
<213> ORGANISM: Artificial sequence
<220> FEATURE:
<223> OTHER INFORMATION: Synthetic peptide

<400> SEQUENCE: 43

Val Gln Ala Thr Gln Ser Asn Gln His Thr Pro Arg Lys
1               5                   10

<210> SEQ ID NO 44
<211> LENGTH: 14
<212> TYPE: PRT
<213> ORGANISM: Artificial sequence
<220> FEATURE:
<223> OTHER INFORMATION: Synthetic peptide

<400> SEQUENCE: 44

Val Gln Ala Thr Gln Ser Asn Gln His Thr Pro Arg Lys Trp
1               5                   10

<210> SEQ ID NO 45
<211> LENGTH: 17
<212> TYPE: PRT
<213> ORGANISM: Artificial sequence
<220> FEATURE:
<223> OTHER INFORMATION: Synthetic peptide

<400> SEQUENCE: 45

Val Gln Ala Thr Gln Ser Asn Gln His Thr Pro Arg Gly Gly Gly Ser
1               5                   10                  15

Lys
```

IMMUNOSTIMULATORY COMPOSITIONS AND USES THEREOF

CROSS REFERENCE

This application claims the benefit of U.S. Provisional Patent Application Nos. 60/542,198 filed Feb. 5, 2004 and 60/633,825 filed Dec. 7, 2004, both of which are hereby incorporated by reference in their entirety.

FIELD OF THE INVENTION

The invention relates to the fields of polypeptides, therapeutics, and immune system activation.

BACKGROUND

Phagocytes such as macrophages and neutrophils provide a primary line of defense against a variety of diseases, including those caused by infectious agents and cancers (Gomme and Bertolini, 2004). During a study of the role of inflammation in development of immunity, Yamamoto and Homma (1991) discovered that a serum protein was required to activate macrophages. This protein is the vitamin D-binding protein (DBP). The human protein is known as group-specific component, or Gc protein. DBP is an abundant, multifunctional, polymorphic glycoprotein in human serum. Highly conserved homologs of this protein occur among all mammalian species (Yang et al., 1990; White and Cooke, 2000). As its name implies, one role of the protein is as a vehicle for circulating vitamin D in blood. Another function involves binding of actin released into the blood during tissue injury. The glycan of the serum protein can be processed to a potent anti-cancer agent, which is expressed through its macrophage activation and anti-angiogenesis activities (Kanda et al., 2002; Gomme and Bertolini, 2004).

DBP is a 458-amino acid protein in humans and consists of three major domains similar to albumin (Head et al., 2002; Otterbein et al., 2002; Verboven et al., 2002). DBP is a glycoprotein that carries a single trisaccharide group (Yang et al., 1985; Cooke and David, 1985). The O-linked glycan is found in the carboxy-terminal Domain III, attached to the hydroxyl group of a specific threonine residue (Thr420 in protein from human). Its structure has been determined as NeuNAc (α2→3) Gal(β1→3) GalNAc(α1→O) Thr, with significant amounts of the O-glycan found only on the Gc1 isoform (Coppenhaver et al., 1983; Viau et al., 1983). Some of the glycans contain a second NeuNAc linked α2→6 to GalNAc. Extensive work by Yamamoto and colleagues (Yamamoto and Kumashiro, 1993; Yamamoto and Naraparaju, 1996 a,b) suggested that DBP has remarkable therapeutic value as an activator of macrophages. Its potent stimulatory activity for macrophage phagocytosis is expressed when its glycosylated site is processed to a single O-linked GalNAc by removal of the NeuNAc (sialic acid) and the Gal residues (Yamamoto and Homma, 1991; Yamamoto and Kumashiro, 1993). The precursor protein can be processed to the active form in vitro by treatment with immobilized sialidase and β-galactosidase (Yamamoto and Kumashiro, 1993; Yamamoto and Naraparaju, 1998). In animals, the modified protein is referred to as DBP-MAF, whereas the active form of the human protein is known as Gc-MAF. These designations are used interchangeably. The active form of the protein reduces tumor cell load (Kisker et al., 2003; Onizuka et al., 2004), provides a therapy against viral infections such as HIV (Yamamoto et al., 1995), and promotes bone growth (Schneider et al., 1995; 2003) and therapy against bone disorders such as ostepetrosis (Yamamoto et al., 1996b). DBP-MAF has also been found to be an effective anti-angiogenesis factor (Kanda et al., 2002; Kisker et al., 2003) and is a potent adjuvant for immunizations (Yamamoto and Naraparaju, 1998). A lectin receptor that specifically binds GalNAc residues was identified on the surface of human macrophages (Iida et al., 1999).

Cancer cells secrete, and some virus particles carry on their surface, an enzymatic activity (N-acetylgalactosaminidase) that depletes the precursor protein in the serum by removing the O-glycoside, which renders the protein inactive as a macrophage activating factor (Yamamoto et al., 1996a, 1997). A decrease in active Gc-MAF may be a major factor in progression of disease. Introduction of the in vitro processed protein leads to dramatic reduction in the amount of cancer cells in animals (Yamamoto and Naraparaju, 1997; Kanda et al., 2002; Kisker et al., 2003; Onizuka et al., 2004) and appears to also reduce the number of HIV particles in infected individuals (Yamamoto et al., 1995). This conclusion is based largely on the decrease in activity of N-acetylgalactosaminidase, whose level appears to be directly correlated with tumor and viral loads in cancer and in HIV-infected patients, respectively (Yamamoto et al., 1997).

SUMMARY OF THE INVENTION

The present invention provides novel immuno-stimulatory polypeptides, and methods for their use and identification. In one aspect, the present invention provides a substantially purified polypeptide with an amino acid sequence comprising at least 10 contiguous amino acids between X1 and X11 of an amino acid sequence according to formula 1:

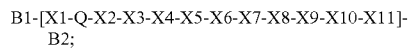
B1-[X1-Q-X2-X3-X4-X5-X6-X7-X8-X9-X10-X11]-B2;

wherein X1 is selected from the group consisting of V, E, and A, or is absent;
 X2 is selected from the group consisting of A, N, and G;
 X3 is any amino acid;
 X4 is selected from the group consisting of P and Q;
 X5 is selected from the group consisting of S, R, and C;
 X6 is selected from the group consisting of N, L, G, and K;
 X7 is selected from the group consisting of Q, A, S, and H;
 X8 is selected from the group consisting of H, L, and A;
 X9 is selected from the group consisting of S and T;
 X10 is selected from the group consisting of P and A;
 X11 is selected from the group consisting of R, G, and P; and
 wherein B1 and B2 are independently 1-5 amino acid residues, or are absent.

In aspect, the present invention provides a substantially purified polypeptide comprising at least 8 contiguous amino acids between X1 and X6 of an amino acid sequence according to formula 2:

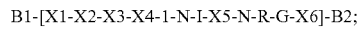
B1-[X1-X2-X3-X4-1-N-I-X5-N-R-G-X6]-B2;

wherein X1 is selected from the group consisting of C, L, and Q, or is absent;
 X2 is selected from the group consisting of R, P, and S or is absent;
 X3 is selected from the group consisting of A, S, and T, or is absent;
 X4 is selected from the group consisting of S and T, or is absent;
 X5 is selected from the group consisting of S and T; and
 X6 is selected from the group consisting of S and T; and
 wherein B1 and B2 are independently 1-5 amino acid residues, or are absent.

In a further aspect, the present invention provides a composition comprising a polypeptide comprising an amino acid sequence of at least 10 contiguous amino acids between X1 and X3 of an amino acid sequence according to formula 3:

B1-[X1-T-D-E-X2-R-R-Q-X3]-B2;

wherein X1 is selected from the group consisting of C and T, or is absent;

X2 is a 4 amino acid group;

X3 is selected from the group consisting of C and P, or is absent; and wherein B1 and B2 are independently 1-5 amino acid residues, or are absent.

In a further aspect, the present invention provides a substantially purified polypeptide comprising a polypeptide that competes with free GalNAc for binding to a GalNAc-specific binding protein, such as GalNAc-specific lectin.

In a further aspect, the present invention provides substantially purified compounds that compete with one or more of the polypeptides according to SEQ ID NOS:1-23, 29, 31-33, and 36-45 for binding to a GalNAc-specific binding protein, such as GalNAc-specific lectin.

In a further aspect, the present invention provides pharmaceutical compositions comprising the substantially purified polypeptides of the invention and a pharmaceutically acceptable carrier.

In a further aspect, the present invention provides a purified nucleic acid composition comprising a nucleic acid sequence that encodes a polypeptide according to the invention, expression vectors comprising the purified nucleic acid, and host cells transfected with the expression vectors.

In a further aspect, the present invention provides methods for stimulating immune system activity in a subject, comprising administering to a subject an amount effective of a polypeptide composition of the invention for stimulating immune system activity.

In a further embodiment, the present invention provides methods for treating a subject with a disorder selected from the group consisting of infections, tumors, bone disorders, immune-suppressed conditions, pain, and angiogenesis-mediated disorders, comprising administering to the subject an amount effective of a polypeptide of the invention.

In a further embodiment, the present invention provides an improved method of vaccination in a subject, comprising administering to a subject receiving a vaccination an amount effective of a polypeptide of the invention for promoting an improved immune system response to the vaccination.

In a further aspect, the present invention provides a method for identifying a GalNAc-polypeptide mimetic, comprising:

a) contacting a plurality of test polypeptides with a GalNAc-specific lectin under conditions to promote binding of the GalNAc-specific lectin with a polypeptide mimetic of GalNAc;

b) removing unbound test polypeptides;

c) repeating steps (a) and (b) a desired number of times;

d) contacting test polypeptides bound to the GalNAc-specific lectin with an amount effective of free GalNAc to displace the bound test polypeptides if the bound test polypeptides are acting as GalNAc-mimetics; and e) identifying those test polypeptides that are displaced from the GalNAc-specific lectin by free GalNAc, wherein such test polypeptides are GalNAc-polypeptide mimetics.

In a further aspect, the present invention provides a method for identifying a GalNAc mimetic compound, comprising:

a) contacting a plurality of test compounds with a GalNAc-specific lectin under conditions to promote binding of the GalNAc-specific lectin with a GalNAc mimetic compound;

b) removing unbound test compounds;

c) repeating steps (a) and (b) a desired number of times;

d) contacting test compounds bound to the GalNAc-specific lectin with an amount effective of a polypeptide comprising of an amino acid sequence according to SEQ ID NOS:1-23, 29, 31-33, and 36-45 to displace the bound test compounds If the bound test compounds are acting as GalNAc-mimetics; and e) identifying those test compounds that are displaced from the GalNAc-specific lectin by a polypeptide comprising of an amino acid sequence according to SEQ ID NOS:1-23, 29, 31-33, and 36-45, wherein such test compounds are GalNAc-mimetic compounds.

BRIEF DESCRIPTION OF THE FIGURES

FIG. 1. Consensus DNA and amino acid sequences derived from phage particles after three rounds of panning of the 12-mer phage display peptide library with a GalNAc-specific lectin.

FIG. 6. Predicted amino acid sequence encoded by the synthetic mimetic gene for Domain III of Gc-MAF, containing 90 amino acids. The mimetic sequence, which was inserted at the site occupied by GalNAc in Gc-MAF, is underlined. Because the N-terminal valine of the consensus sequence (VQATQSNQHTPR) does not seem to be required for mimetic activity (see Table 1), the terminal V was replaced with the N-terminal region of Domain III. The spacer sequence (GGGS, see FIG. 1) was included, but the KW-biotin sequence (see FIG. 2) was replaced with the C-terminal region of Domain III. The nucleic acid sequence was optimized for expression in *Escherichia coli* and the chloroplast of *Chilanydomonas reinhardtii* (SEQ ID NO: 31).

FIG. 7. Response of adherent peripheral blood cells to mimetic peptides. Reduction of cytochrome c by superoxide anion radical is indicated by an increase in absorbance (OD), whereas a loss of absorbance indicates destruction of the cytochrome. (A) Total adherent cells from 300 μl of blood were assayed. Samples 1 and 2 contained 5 nM and 2.5 nM branched mimetic peptide, respectively. Samples 3 and 4 contained 5 nM and 2.5 nM linear mimetic peptide, respectively. Sample 5 contained 50 ng/ml lipopolysaccharide (weight equivalent to 6 nM peptide). Sample 6, untreated control cells. (B) Adherent cells were scraped from the surface and $1\times10^5$ cells were placed in each well. The assay was performed as in (A). Samples 1 and 2 contained 10 nM and 5 DM mimetic peptide, respectively. Samples 3 and 4 contained 10 nM and 5 DM linear peptide, respectively. Sample 5 contained 50 ng/ml lipopolysaccharide. Sample 6, untreated control cells.

FIG. 10 Amino acid sequence of SEQ ID NO:29.

FIG. 11 Amino acid sequence of SEQ ID NO:31.

DETAILED DESCRIPTION OF THE INVENTION

Figure 2:
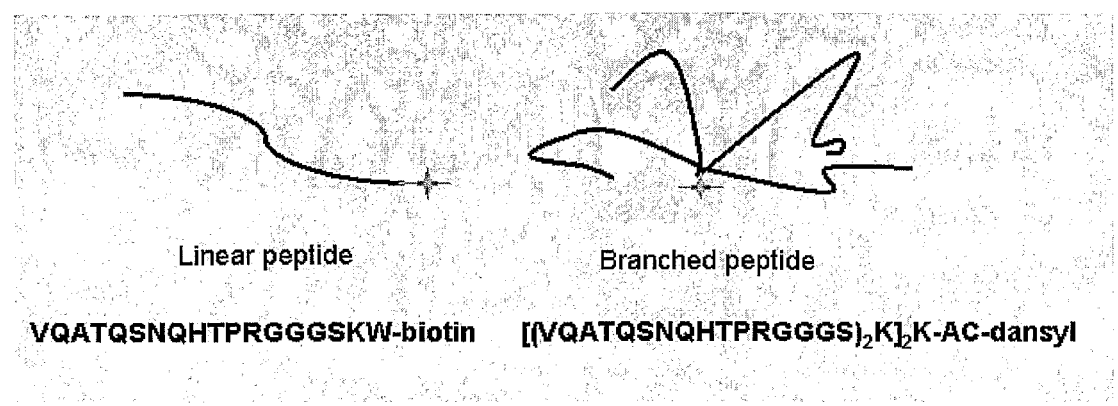
FIG. 2. Diagrammatic representations and amino acid sequences of the linear and branched peptide mimetic structures. The star symbols indicate the position of the reporter residue at the C-terminus of the structures.

Within this application, unless otherwise stated, the techniques utilized may be found in any of several well-known references such as: *Molecular Cloning: A Laboratory Manual* (Sambrook, et al., 1989. Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., 1990. Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), and *Gene Transfer and Expression Protocols*, pp. 109-128, E. J. Murray, ed. (1991). The Humana Press Inc., Clifton, N.J.).

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; W is tryptophan; and Y is tyrosine.

As used herein, the singular forms "a", "an" and "the" include plural referents unless the context clearly dictates otherwise. For example, reference to a "polypeptide" means one or more polypeptides.

The inventors have identified a series of polypeptide mimetics of GalNAc, using methods described herein. Such mimetics act as immunostimulatory compounds and can be used for the various methods of the invention described below. Thus, in a first aspect, the present invention provides a substantially purified polypeptide which comprises or consists of at least 10 contiguous amino acids between X1 and X11 of an amino acid sequence according to formula 1:

B1-[X1-Q-X2-X3-X4-X5-X6-X7-X8-X9-X10-X11]-B2;

wherein X1 is selected from the group consisting of V, E, and A, or is absent;
X2 is selected from the group consisting of A, N, and G;
X3 is any amino acid;
X4 is selected from the group consisting of P and Q;
X5 is selected from the group consisting of S, R, and C;
X6 is selected from the group consisting of N, L, G, and K;
X7 is selected from the group consisting of Q, A, S, and H;
X8 is selected from the group consisting of H, L, and A;
X9 is selected from the group consisting of S and T;
X10 is selected from the group consisting of P and A;
X11 is selected from the group consisting of R, G, and P; and
wherein B1 and B2 are independently 1-5 amino acids, or are absent,
or functional equivalents thereof.

In a preferred embodiment of the substantially purified polypeptide of this first aspect of the invention,
X1 is V or is absent;
X2 is selected from the group consisting of A and N
X5 is selected from the group consisting of S and R;
X6 is N;
X7 is selected from the group consisting of Q and A;
X8 is selected from the group consisting of H and L; and
X11 is selected from the group consisting of R and G.

In a further preferred embodiment of the substantially purified polypeptide of this first aspect of the invention,
X1 is V or is absent;
X2 is A;
X3 is any amino acid;
X4 is Q;
X5 is S;
X6 is N;
X7 is Q;
X8 is H;
X9 is T;
X10 is P; and
X11 is R.

In a still further preferred embodiment of the substantially purified polypeptide of this first aspect of the invention, X3 is T.

In a further preferred embodiment of each of the above embodiments of this first aspect of the invention, the substantially purified polypeptide comprises or consists of 11 or 12 contiguous amino acids between X1 and X11 of an amino acid sequence according to formula 1.

Specific examples of polypeptides falling within this genus are identified in the examples below, and also include, but are not limited to:

| | |
|---|---|
| QATQSNQHTPR | (SEQ ID NO: 36) |
| QATQSNQHTPRGGGS | (SEQ ID NO: 37) |
| VQATQSNQHTPRGGGS | (SEQ ID NO: 38) |
| QATQSNQHTPRK | (SEQ ID NO: 39) |
| QATQSNQHTPRKW | (SEQ ID NO: 40) |
| QATQSNQHTPRGGGSK | (SEQ ID NO: 41) |
| QATQSNQHTPRGGGSKW | (SEQ ID NO: 42) |

-continued

| | |
|---|---|
| VQATQSNQHTPRK | (SEQ ID NO: 43) |
| VQATQSNQHTPRKW | (SEQ ID NO: 44) |
| VQATQSNQHTPRGGGSK | (SEQ ID NO: 45) |

In a second aspect, the present invention provides a substantially purified polypeptide comprising or consisting of at least 8 contiguous amino acids between X1 and X6 of an amino acid sequence according to formula 2:

B1-[X1-X2-X3-X4-1-N-I-X5-N-R-G-X6]-B2;

wherein X1 is selected from the group consisting of C, L, and Q, or is absent;
X2 is selected from the group consisting of R, P, and S or is absent;
X3 is selected from the group consisting of A, S, and T, or is absent;
X4 is selected from the group consisting of S and T, or is absent;
X5 is selected from the group consisting of S and T; and
X6 is selected from the group consisting of S and T; and
wherein B1 and B2 are independently 1-5 amino acids, or are absent,
or functional equivalents thereof.

In a preferred embodiment of this second aspect of the invention,
X1 is L or is absent;
X2 is P or is absent;
X3 is T or is absent;
X4 and X5 are T; and
X6 is S.

In various preferred embodiments of each of these embodiments of the second aspect of the invention, the substantially purified polypeptides comprise or consist of at least 9, 10, 11, or 12 contiguous amino acids between X1 and X6 of an amino acid sequence according to formula 2. Specific examples of polypeptides falling within this genus are identified in the examples below.

In a third aspect, the present invention provides a substantially purified polypeptide comprising or consisting of a polypeptide of at least 9 contiguous amino acids between X1 and X3 of an amino acid sequence according to formula 3:

B1-[X1-T-D-E-X2-R—R-Q-X3]-B2;

wherein X1 is selected from the group consisting of C and T, or is absent;
X2 is a 4 amino acid group;
X3 is selected from the group consisting of C and P, or is absent; and
wherein B1 and B2 are independently a peptide of 1-5 amino acids, or are absent,
or functional equivalents thereof.

In a preferred embodiment of this third aspect of the invention, X2 consists of an amino acid sequence according to general formula 4:

Z1-Z2-Z3-Z4 wherein Z1 is selected from the group consisting of A and P;
Z2 is selected from the group consisting of L and F;
Z3 is selected from the group consisting of Y and V; and
Z4 is selected from the group consisting of T and Y.

In various preferred embodiments of each of these embodiments of the third aspect of the invention, the substantially purified polypeptide comprises or consists of at least 10, 11 or 12 contiguous amino acids between X1 and X3 of an amino acid sequence according to formula 3. Specific examples of polypeptides falling within this genus are identified in the examples below.

In each of the first through third aspects of the invention, the B1 and B2 groups are optionally present, for example, to provide appropriate spacing for branched embodiments of the polypeptides, as described below.

In a fourth aspect, the present invention provides a substantially purified polypeptide that competes with free GalNAc for binding to a GalNAc-specific binding protein, such as GalNAc-specific lectin. Such lectins include those purified from *Helix pomatia, Vicia villosa,* or *Robinia pseudoacacia,* or functional equivalents thereof (commercially available, for example, from Sigma Chemical Co., St. Louis, Mo.). Additional GalNAc-specific lectins include but are not limited to the following: *Bauhinia Purpurea* Lectin (BPL), *Dolichos Biflorus* Lectin (DBA), *Griffonia Simplicifolia* Lectin (GSL I—isolectin B4), *Maculura Pomifera* Lectin (MPL), *Psophocarcpus Tetragonolobus* Lectin (PTL), *Ricinus Communis* Agglutnin (RCA) I 120 and II 60, *Saphora Japonica* Agglutnin (SJA), *Soybean Agglutnin* (SBA), *Wisteria Floribunda* Agglutinin (WFA). Additional commercial sources of these lectins include the following: Alexis Platform, Reacto Labs, USBiological, Vector Labs, Molecular Probes, Biotrend, Chemikalien GmbH, Invitrogen Corp., Seikagulku America, EY Laboratories, Calbiochem, AlerCheck, Pierce, Accurate Chemical and Scientific Corp., MoBiTec, GALAB, Merck Biosciences, UK, Gentaur France, Biomeda, and Honen Corp, Japan.

The crystal structure of GalNAc-specific lectins from *Robinia pseudoacacia* (Rabijns et al., 2001) and from *Vivia villosa* were published (Babino et al., 2003). These structures are examples of the highly conserved sugar-binding sites of plant lectins (Loris et al., 1998). The critical amino acids in the polypeptide segments that form the carbohydrate-binding site are highly conserved among plant lectins, including those specific for GalNAc or Gal (Osinaga et al., 1997). As an example, the GalNAc-specific binding site in the *Vicia villosa* lectin is formed on the surface of the protein by four loops that contain the amino acids aspartate-85, glycine-103, tyrosine-127, asparagine-129, tryptophan-131 and leucine-213, which interact with functional groups on the sugar (Babino et al., 2003). A conserved aspartate-90 interacts with a divalent cation. Another GalNAc-specific lectin from *Robinia pseudoacacia* (black locust) has a binding site containing similar amino acid residues, e.g., aspartate-87, glycine-104. glycine-105, phenylalanine-129, asparagine-131, isoleucine-216 and aspartate-217 (Rabijns et al., 2001). A lectin that is highly specific for GalNAc, purified from the sea cucumber *Cucumaria echinata* and characterized (Sugawara et al., 2004), contains a similar group of amino acids such as glutamine-101, aspartate-103, tryptophan-105, glutamate-109, arginine-115 and asparagine-123 that interact with the sugar. These amino acids are also found in the GalNAc-binding site of a rat hepatic lectin, RHL-1 (Kolatkar et al., 1998). Various lectins may contain bound divalent cations and are thus designated C-type lectins. This class of proteins may or may not include specific divalent cations as part of their structure. Any protein, produced by any species or made synthetically, that binds GalNAc in a specific manner is appropriate for use in this technology.

In a preferred embodiment of this fourth aspect of the invention, the polypeptide comprises an amino acid sequence selected from the group consisting of SEQ ID NOS:1-23, 29, 31-33, and 36-45.

Competition for binding of GalNAc to GalNAc-specific lectins by test polypeptides can be determined by any suitable technique. For example, the GalNAc-specific lectin can be incubated first with the test polypeptide, and then with the GalNAc. The test polypeptide competes with the GalNAc if GalNAc binding to the GalNAc-specific lectin is 90% or less than its binding in the absence of the test polypeptide, more preferably if GalNAc binding to the GalNAc-specific lectin is 80%, 70%, 60%, 50%, 40%, 30%, 20%, or 10% or less than its binding in the absence of the test polypeptide. The desired level of competitive activity of a test polypeptide can be selected for, as will be apparent to those of skill in the art. Similarly, as will be apparent to those of skill in the art, the GalNAc-specific lectin can be incubated first with the GalNAc, and then with the test polypeptide and competition can be assayed as discussed above. Conditions should be suitable to promote binding, as described in the Examples below. Typically, physiological or near-physiological conditions are suitable for GalNAc binding to GalNAc-specific lectins, for example, room temperature in a buffer solution composed of 50 mM Tris-HCl, pH 7.5, containing 150 mM NaCl, 1 mM $CaCl_2$, 1 mM $MnCl_2$ and 1 mM $MgCl_2$. GalNAc and the GalNAc-specific binding protein can be used in these assays in any amount suitable for the specific assay conducted, preferably between 1 nM and 5001 nM; more preferably between 10 nM and 500 mM, even more preferably between 100 nM and 100 mM.

Several variables are explored to optimize binding of phage particles to the lectin. (1) Detergents are used to reduce nonspecific interactions. Stringency can be increased by increasing the concentration of detergents such as Tween-20, Triton X100, dodecyl maltoside, etc. (2) Temperature can be varied between 4° C. and 55° C. An increase in temperature may cause an increase or decrease in stringency, depending on the specific characteristics of the interaction. (3) The time of the binding step and the elution step can be adjusted to select for differences in the 'on' rates and 'off' rates. Because equilibrium factors apply to the interactions, complex formation can also be altered by concentrations of the reactants such as the target lectin. Displacement of phage particles from the lectin by addition of free GalNAc is also concentration dependent. These factors can be adjusted to provide optimal results. (4) With each round of panning, phage particles with a specific sequence are enriched. Panning is continued until most of the eluted particles contain a consensus binding sequence. With high stringency conditions, three rounds of palming are usually sufficient. Detailed data on the binding characteristics are then determined by specific binding assays with synthetic peptides.

In a fifth aspect, the present invention provides a substantially purified compound that competes with one or more of the polypeptides comprising or consisting of an amino acid sequence according to one or more of SEQ ID NOS:1-23, 29, 31-33, and 36-45 for binding to a GalNAc-specific protein, such as GalNAc-specific lectin, or functional equivalents thereof. Competition for binding of the polypeptide of any one of SEQ ID NOS:1-23, 29, 31-33, and 36-45 to GalNAc-specific lectins by test compounds can be determined by any suitable technique, similar to the competition techniques described above, with the GalNAc being replaced by one or more of the polypeptides comprising or consisting of an amino acid sequence according to one or more of SEQ ID NOS:1-23, 29, 31-33, and 36-45, and thus each of the various embodiments of the fourth aspect of the invention is also applicable to this fifth aspect of the invention. The test compounds in this fifth aspect of the invention can comprise small molecules, nucleic acids, or polypeptides, such as those found in various commercially available compound libraries. In a preferred embodiment of this fifth aspect, the test compounds comprise polypeptides. The polypeptides comprising or consisting of an amino acid sequence according to one or more of SEQ ID NOS:1-23, 29, and 31-33 can be used in these assays in any amount suitable for the specific assay conducted, preferably between 1 nM and 500 mM; more preferably between 10 nM and 500 nM, even more preferably between 100 nM and 100 mM.

As used in each of the aspects and embodiments of the invention herein, the term "substantially purified" means that the polypeptides (or nucleic acids) of the invention are substantially free of cellular material, gel materials, culture medium, and contaminating polypeptides or nucleic acids (such as from nucleic acid libraries or expression products therefrom), except as described herein, when produced by recombinant techniques; or substantially free of chemical precursors or other chemicals when chemically synthesized, except as described herein.

Each of the above aspects and embodiments of the substantially purified polypeptides and compounds of the invention act as mimetics of GalNAc, and thus can be used as immunostimulatory compounds and for the various methods of the invention described below.

As used in each of the aspects and embodiments of the invention herein, the term "polypeptide" is used in its broadest sense to refer to a sequence of subunit amino acids, amino acid analogs, or peptidomimetics. The subunits are linked by peptide bonds, except where noted. The polypeptides described herein may be chemically synthesized or recombinantly expressed, and may be present in a single copy, or in multiple copies (2 or more copies, preferably between 2 and 10; more preferably between 2 and 5 copies). In one non-limiting example, multiple copies of the polypeptide are present in a branched configuration by methods known to those of skill in the art and as disclosed herein, such as *Solid Phase Peptide Synthesis: A Practical Approach* (B. Atherton and R. C. Sheppard, eds., 1989. Oxford University Press, New York, N.Y.); *Solid-Phase Synthesis: A Practical Guide* (S. A. Kates and F. Albericio, eds., 2000. Marcel Dekker, Inc., New York, N.Y.); *Fmoc Solid Phase Peptide Synthesis: A Practical Approach* (W. C. Chan and P. D. White, eds., 2000. Oxford University Press, New York, N.Y.). Technology for synthesis of branched peptides is found in D. N. Posnett, H. McGrath and J. P. Tam (1988) "A novel method for producing anti-peptide antibodies." *Journal of Biological Chemistry* 263: 1719-1725.

The Tn determinant (GalNAc-α-O-Serine/Threonine) is a cryptic antigen that is "covered" on the surface of normal cells but expressed on many human tumor-associated structure (Babino et al., 2003). Lo-Man et al. (1999, 2001, 2004) proposed that antibodies against the Tn antigen should be effective therapeutic tools against cancers. These investigators have shown that clusters of GalNAc at the termini of branched structures elicit strong immunogenic responses. Clusters of the sugar show very different behavior than single residues (Iida et al., 1999; Vichier-Guerre et al., 2000). A synthetic multiple-antigen glycopeptide was shown to be immunogenic in mice and the presence of the antibodies partially protected mice from transplanted tumor cells. The branched molecule with GalNAc residues at the terminus of each branch, or a structure with three GalNAc residues at the terminus of each branch (Lo-Man et al., 2001), are strong antigenic structures, approximately $10^6$-fold more antigenic than a molecule with a single antigen (Lo-Man et al., 1999; Vichier-Guerre et al., 2000). A human macrophage C-type lectin binds GalNAc-containing peptides with high specificity, including the Tn antigen, which is structurally similar to the active site of Gc-MAF. Glycopeptides containing multiple, closely clustered Tn determinants were bound by the lectin with up to 38-fold greater affinity than a single GalNAc attached to the peptide (Iida et al., 1999). The data indicate that the perferred binding of glycopeptides to the human macrophage lectin is as the trimeric protein (Iida et al., 1999), which is similar to observations that monoclonal antibodies recognize clustered GalNAc residues. Thus clustering of the antigen is required for recognition by antibodies and the clusters are more effective in stimulating macrophages than single Tn molecules. The basic design to these structures is similar to the branched mimetic shown in FIG. 2, and these results support the design of the mimetic polpeptide structure of this invention. In contrast to the GalNAc-bearing polypeptides, no adverse immunogenic response has been detected thus far to the mimetic polypeptide of this invention.

Where multiple copies of the polypeptides of the invention are present, the multiple copies can be multiple copies of the same polypeptide, or may include two or more different polypeptides, such as a branched multimer incorporating the polypeptide of SEQ ID NO:3 and SEQ ID NO:6, as disclosed below. Those of skill in the art will understand that many such permutations are possible based on the teachings of the present invention.

Preferably, the substantially purified polypeptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (N-α-amino protected N-α-t-butyloxycarbonyl) amino acid resin with the standard deprotecting, neutralization, coupling and wash protocols of the original solid phase procedure of Merrifield (1963, J. Am. Chem. Soc. 85:2149-2154), or the base-labile N-α-amino protected 9-fluorenylmethoxycarbonyl (Fmoc) amino acids first described by Carpino and Han (1972, *Journal of Organic Chemistry* 37:3403-3409). Both Fmoc and Boc N-α-amino protected amino acids can be obtained from Sigma-Aldrich, Cambridge Research Biochemical, or other chemical companies familiar to those skilled in the art. In addition, the polypeptides can be synthesized with other N-α-protecting groups that are familiar to those skilled in this art.

Solid phase peptide synthesis may be accomplished by techniques familiar to those in the art and provided, for example, in Stewart and Young (1984) *Solid Phase Synthesis*, Second Edition, Pierce Chemical Co., Rockford, Ill.; Fields and Noble (1990) *Internatian Journal of Peptide and Protein Research* 35:161-214, or using automated synthesizers. The substantially purified polypeptides of the invention may comprise D-amino acids (which are resistant to L-amino acid-specific proteases in vivo), a combination of D- and L-amino acids, and various "designer" amino acids (e.g., β-methyl amino acids, C-α-methyl amino acids, and N-α-methyl amino acids, etc.) to convey special properties. Synthetic amino acids include ornithine for lysine, and norleucine for leucine or isoleucine.

In addition, the substantially purified polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

The substantially purified polypeptides of the invention may also be present as part of a fusion protein, in which case it may be desirable to synthesize the polypeptide using recombinant DNA technology. Such fusion proteins may include, for example, fusion with peptide transduction domains to permit movement of a fusion protein with the polypeptides of the invention to pass the cell membrane. As used herein, the term "transduction domain" means one or more amino acid sequence or any other molecule that can carry the active domain across cell membranes. These domains can be linked to other polypeptides to direct movement of the linked polypeptide across cell membranes. In some cases the transducing molecules do not need to be covalently linked to the active polypeptide. In a preferred embodiment, the transduction domain is linked to the rest of the polypeptide via peptide bonding. (See, for example, *Cell* 55: 1179-1188, 1988; *Cell* 55: 1189-1193, 1988; *Proc. Natl. Acad. Sci. USA* 91: 664-668, 1994; *Science* 285: 1569-1572, 1999; *J. Biol. Chem.* 276: 3254-3261, 2001; and *Cancer Res* 61: 474-477, 2001).

In another example, the polypeptides of the invention may be present in a fusion protein with full length DBP, or with variations of Domain III of DBP (including but not limited to polypeptides comprising the amino acid sequence of SEQ. ID NOS: 29 and 31), as described in more detail below.

In a further example, the polypeptides of the invention can be fused or otherwise linked to therapeutic agents in order to enhance potential therapeutic effects of both agents. For example, monoclonal antibodies have been generated against a large number of cancers and other pathogenic agents for therapeutic use. Binding of these antibodies to the infectious agent is the first part of the therapy; phagocytosis of the antibody-bound agent by macrophages must occur to eliminate the agent from the body. Therefore, a combination of target-directed antibodies plus the polypeptides of the present invention would be an effective combination therapy. Many other such fusions or linkages to other therapeutic agents will be apparent to those of skill in the art based on the teachings herein.

It will be understood by those of skill in the art that such fusion proteins can comprise the addition of a polypeptide of the invention to the carboxy or amino terminal end of another polypeptide, or can comprise the placement of a polypeptide of the invention within another polypeptide, such as that described in the Examples below. Those of skill in the art will recognize many such fusion proteins that can be made and used according to the teachings of the present invention.

The substantially purified polypeptides of the invention may be modified by, or combined with, non-polypeptide compounds to produce desirable characteristics, such modifications including but not limited to PEGylation with polyethylene glycol to improve in vivo residency time of the polypeptide, alkylation, phosphorylation, acylation, ester formation, amide formation, lipophilic substituent addition, and modification with markers including but not limited to fluorophores, biotin, dansyl derivatives, and radioactive moieties. Such compounds can be directly linked, or can be linked indirectly, for example via a spacer including but not limited to the B1 and/or B2 groups of general formulas 1-3 of the present invention, β-alanine, gamma-aminobutyric acid (GABA), L/D-glutamic acid, and succillic acid.

In a sixth aspect, the present invention provides pharmaceutical compositions, comprising one or more of the polypeptides disclosed herein, and a pharmaceutically acceptable carrier. Such pharmaceutical compositions are especially useful for carrying out the methods of the invention described below. For administration, the polypeptides are ordinarily combined with one or more adjuvants appropriate for the indicated route of administration. The compounds may be admixed with alum, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in physiological saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The polypeptides may be linked to other compounds to promote an increased half-life in vivo, such as polyethylene glycol. Such linkage can be covalent or non-covalent as is understood by those of skill in the art.

In a seventh aspect, the present invention provides substantially purified nucleic acid sequences encoding the polypeptides of the present invention, or functional equivalents thereof. Appropriate nucleic acid sequences according to this aspect of the invention will be apparent to one of skill in the art based on the disclosure provided herein and the general level of skill in the art. In various preferred embodiments, the nucleic acid sequences comprise or consist of a nucleic acid sequence that encodes the amino acid according to SEQ ID NOS:1-23, 29, 31-33, and 36-45.

In an eighth aspect, the present invention provides expression vectors comprising DNA control sequences operably linked to the isolated nucleic acid molecules of the present invention, as disclosed above, or functional equivalents thereof. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited to plasmid and viral-based expression vectors.

In a ninth aspect, the present invention provides genetically engineered host cells comprising the expression vectors of the invention, or functional equivalents thereof. Such host cells can be prokaryotic cells or eukaryotic cells, and can be either transiently or stably transfected, or can be transduced with viral vectors. For example, such host cells can be bacterial cells (such as *E. coli*) or algal cells (such as *Chlamydomonas reinhardtii*), which do not generally glycosylate proteins. Thus, in one embodiment, bacterial, plant, or algal cells can be transfected with an expression vector expressing Domain III or full length DBP as a fusion with a polypeptide of the invention, to provide more efficient production of active Domain III or DBP in a non-maimalian system, as described below.

Thus, in a further embodiment of this ninth aspect, the invention provides improved methods for producing active Domain III and DBP analogs, comprising transfecting a bacterial, plant, or algal cell with an expression vector that expresses a fusion protein comprising (a) Domain III or DBP; and (b) a polypeptide according to the present invention, and isolating the fusion protein, wherein the fusion protein is a non-glycosylated but active DBP or Domain III analog. In a preferred embodiment, the fusion protein comprises or consists of an amino acid sequence selected from the group consisting of SEQ ID NOS:29 and 31, or functional equivalents thereof. In a further preferred embodiment, the expression vector comprises or consists of a nucleic acid sequence selected from the group consisting of SEQ ID NOS:28 and 30, or functional equivalents thereof. Methods for isolating recombinant proteins from bacterial, plant, and algal cells is well known to those of skill in the art. This preferred embodiment also provides transgenic plants containing the expression vectors of the invention. For transferring the DNA into the plant cells, plant explants may suitably be co-cultivated with *Agrobacteriuin tuinefaciens* or *Agrobacterium rhizogeines*. From the infected plant material (e.g., pieces of leaves, stem segments, roots, protoplasts or suspension-cultivated plant cells), whole plants may then be regenerated in a suitable medium which may contain antibiotics or biozides for the selection of transformed cells. The plants obtained in such a way may then be examined as to whether the introduced DNA is present or not. Other possibilities for introducing foreign DNA, such as using the biolistic method or by transforming protoplasts are known to the skilled person [cf. e.g. Willmitzer, L. (1993) Transgenic plants. In: *Biotechnology, A Multi-Volume Comprehensive Treatise* (H. J. Rehm, G. Reed, A. Puhler, P. Stadler, editors), Vol. 2, 627-659, VCH Weinheim-New York-Basel-Cambridge].

In a tenth aspect, the present invention provides methods for stimulating immune system activity in a subject, comprising administering to a subject an amount effective of a polypeptide according to the invention for stimulating immune system activity.

As used herein the phrase "stimulating immune system activity" means to increase the activity of one or more components of the immune system, including phagocytes, macrophages, and neutrophils. Substances secreted by activated macrophages in turn stimulate other cells of the immune system, in particular dendritic cells. As such, methods for stimulating immune system activity are broadly useful for treating cancer, viral infections, angiogenesis-mediated disorders, bone disorders, immune-suppressed disorders, pain, and as adjuvants for vaccinations.

Thus, in an eleventh aspect, the present invention provides methods for treating one or more disorders in a subject, selected from the group consisting of viral infection, cancer, bone disorders, immune suppressed disorder, pain, and angiogenesis-mediated disorders, comprising administering to a subject an amount effective of a polypeptide according to the invention for treating the disorder.

In a twelfth aspect, the present invention provides methods for promoting an improved immune system response to a vaccination, comprising administering to a subject receiving a vaccination an amount effective of a polypeptide according to the invention for promoting an improved immune system response to the vaccination. In carrying out the methods for promoting an improved immune system response to the vaccination according to the present invention, the polypeptides, or pharmaceutical compositions thereof, of the invention can be administered before, simultaneously with, or after vaccine administration. Where the vaccine is administered on multiple occasions, the polypeptides of the invention can be administered together with a single vaccine administration, or with multiple vaccine administrations. In a preferred embodiment, the polypeptides are administered simultaneously with the one or more rounds of vaccination. Preferred classes of patients include populations at high risk for viral infection, including but not limited to children, health care workers, senior citizens, and those at high risk of specific types of viral infection, such as partners of HIV infected individuals, sex trade workers, and intravenous drug users.

In a preferred embodiment of the tenth, eleventh, and twelfth aspects of the invention, the subject is a mammal; in a more preferred embodiment, the subject is a human.

In various embodiments of the tenth, eleventh, and twelfth aspects of the invention, administration of the polypeptide is accomplished via direct delivery (for example, by injection), or by gene therapy via administration of an appropriate expression vector of the invention which can be expressed in the target tissue. In embodiments employing gene therapy, it is preferred to use viral expression vectors, including but not limited to adenoviral and retroviral vectors.

In carrying out the methods of the invention, the polypeptides or pharmaceutical compositions thereof may be made up in a solid form (including granules, powders, transdermal or transmucosal patches or suppositories) or in a liquid form (e.g., solutions, suspensions, or emulsions), and may be subjected to conventional pharmaceutical operations such as sterilization and/or may contain conventional adjuvants, such as stabilizers, wetting agents, emulsifiers, preservatives, cosolvents, suspending agents, viscosity enhancing agents, ionic strength and osmolality adjustors and other excipients in addition to buffering agents. Suitable water soluble preservatives which may be employed in the drug delivery vehicle include sodium bisulfite, sodium thiosulfate, ascorbate, benzalkonium chloride, chlorobutanol, thimerosal, phenylmercuric borate, parabens, benzyl alcohol, phenylethanol or antioxidants such as Vitamin E and tocopherol and chelators such as EDTA and EGTA. These agents may be present, generally, in amounts of about 0.001% to about 5% by weight and, preferably, in the amount of about 0.01 to about 2% by weight.

For administration, the polypeptides are ordinarily combined with one or more adjuvants appropriate for the indicated route of administration. The polypeptides may be admixed with alum, lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the polypeptides of this invention may be dissolved in physiological saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

For use herein, the polypeptides may be administered by any suitable route, including local delivery, parentally, transdermally, by inhalation, or topically in dosage unit formulations containing conventional pharmaceutically acceptable carriers, adjuvants, and vehicles. The term parenteral as used herein includes, subcutaneous, intravenous, intramuscular, intrasternal, intratendinous, intraspinal, intracranial, intrathoracic, infusion techniques or intraperitoneally. Suppositories for rectal administration of the active agents in combination with the vaccines can be prepared by mixing the drug with a suitable non-irritating excipient such as cocoa buffer and polyethylene glycols which are solid at ordinary temperatures, but liquid at the rectal temperature and will therefore melt in the rectum and release the drug.

Solid dosage forms for oral administration may include capsules, tablets, pills, powders and granules. In such solid dosage forms, the polypeptides may be admixed with at least one inert diluent such as alum, sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings. Liquid dosage forms for oral administration may include pharmaceutically acceptable emulsions, solutions, suspensions, syrups and elixirs containing inert diluents commonly used in the art, such as water. Such compositions may also comprise adjuvants, such as wetting agents, emulsifying and suspending agents and sweetening, flavoring and perfuming agents.

As used herein for all of the methods of the invention, an "amount effective" of the polypeptides is an amount that is sufficient to provide the intended benefit of treatment. An effective amount of the polypeptides that can be employed ranges generally between about 0.01 µg/kg body weight and about 10 mg/kg body weight, preferably ranging between about 0.05 µg/kg and about 5 mg/kg body weight. However, dosage levels are based on a variety of factors, including the type of disorder, the age, weight, sex, medical condition of the individual, the severity of the condition, the route of administration, and the particular compound employed. Thus, the dosage regimen may vary widely, but can be determined routinely by a physician using standard methods.

Tumors susceptible of treatment by the methods of the invention include lymphomas, sarcomas, melanomas, neuroblastomas, carcinomas, leukemias, and mesotheliomas. Methods of tumor treatment according to the invention can be used in combination with surgery on the subject, wherein surgery includes primary surgery for removing one or more tumors, secondary cytoreductive surgery, and palliative secondary surgery. In a further embodiment, the methods further comprise treating the subject with chemotherapy and/or radiation therapy, which can reduce the chemotherapy and/or radiation dosage necessary to inhibit tumor growth and/or metastasis. As used herein, "radiotherapy" includes but is not limited to the use of radio-labeled compounds targeting tumor cells. Any reduction in chemotherapeutic or radiation dosage benefits the patient by resulting in fewer and decreased side effects relative to standard chemotherapy and/ or radiation therapy treatment. In this embodiment, the polypeptide may be administered prior to, at the time of, or shortly after a given round of treatment with chemotherapeutic and/or radiation therapy. In a preferred embodiment, the polypeptide is administered prior to or simultaneously with a given round of chemotherapy and/or radiation therapy. In a most preferred embodiment, the polypeptide is administered prior to or simultaneously with each round of chemotherapy and/or radiation therapy. The exact timing of compound administration will be determined by an attending physician based on a number of factors, but the polypeptide is generally administered between 24 hours before a given round of chemotherapy and/or radiation therapy and simultaneously with a given round of chemotherapy and/or radiation therapy. The tumor treating methods of the invention are appropriate for use with chemotherapy using one or more cytotoxic agent (ie., chemotherapeutic), including, but not limited to, cyclophosphamide, taxol, 5-fluorouracil, adriamycin, cisplatinum, methotrexate, cytosine arabinoside, mitomycin C, prednisone, vindesine, carbaplatinum, and vincristine. The cytotoxic agent can also be an antiviral compound which is capable of destroying proliferating cells. For a general discussion of cytotoxic agents used in chemotherapy, see Sathe, M. et al. (1978) *Cancer Chemotherapeutic Agents: Handbook of Clinical Data*, hereby incorporated by reference. When administered as a combination, the therapeutic agents can be formulated as separate compositions that are given at the same time or different times, or the therapeutic agents can be given as a single composition. The methods of the invention are also particularly suitable for those patients in need of repeated or high doses of chemotherapy and/or radiation therapy.

The production of the Tn antigen in cancer patients may lead to an inflammatory reaction that occurs as the result of antibody-antigen complex formation. Thus, while not being bound by any specific mechanism of action, the dramatic improvement in quality of life as the result of treatment with the branched peptide mimetic (see the examples below) may result from physiological effect resulting from competition between the polypeptide and the Tn antigen for the antibodies.

Any infection to which the immune system responds can be treated according to the methods of the invention. Infections, as used herein, are broadly defined to mean situations when the invasion of a host by an agent is associated with the clinical manifestations of infection including, but not limited to, at least one of the following: abnormal temperature, increased heart rate, abnormal respiratory rate, abnormal white blood cell count, fatigue, chills, muscle ache, pain, dizziness, dehydration, vomiting, diarrhea, organ dysfunction, and sepsis. Such infections may be bacterial, viral, parasitic, or fungal in nature. The method may further comprise combinatorial treatment with other anti-infective agents, such as antibiotics. Viruses susceptible to treatment according to the methods of the invention include, but are not limited to adenoviruses, rhinoviruses, rabies, murine leukemia virus, poxviruses, lentiviruses, retroviruses; including disease-causing viruses such as human immunodeficiency virus, hepatitis A and B viruses, herpes simplex virus, cytomegalovirus, human papilloma virus, coxsackie virus, smallpox, hemorrhagic virus, ebola, and human T-cell-leukemia virus. Bacteria susceptible to treatment include, but are not limited to gram negative bacteria and gram-positive bacteria, including but not limited to *Escherichia coli, Staphylococcus aureus, Staphylococcus epidermidis, Streptococcus pneumoniae, Mycobacterium tuberculosis, Neisseria gonorrhoeae, Neisseria meningitis, Bordetalla pertussis, Salmonella thyhimurium, Salmonella choleraesuis*, and *Enterobacter cloacae*, as well as bacterium in the genus *Acinetobacter, Actinomyes, Bacilus, Bordetella, Borrelia, Brocella, Clostridium, Corynebacterium, Campylobacter, Deincoccus, Escherichia, Enterobacter, Enterrococcus, Eubacterium, Flavobacterium, Francisella Glueonobacter, Heliobacter, Intrasporangium, Janthinobacterium, Klebsiella, Kingella, Legionella, Leptospira, Mycobacterium, Moraxella, Neisseria, Oscillospira, Proteus, Psendomonas, Providencia, Rickettsia, Salomonella, Staphylococcus, Shigella, Spirilum, Streptococcus, Treponema, Ureplasma, Vibrio, Wolinella, Wolbachia, Xanthomonas, Yersinis*, and *Zoogloea* Parasitic agents that can be treated by the methods of this aspect of the invention include, but are not limited to *Plasmodium, Leishmania, Trypanosomes, Trichomona*, and including but not limited to parasitic agents in the phylums *Acanthocephela, Nematoda, Nemtomorpha, Platyhelminthes, Digena, Eucestoda, Turbellaria, Sarcomastigophora* and *Protozoa* including but not limited to species *Giardia duodenalis, Cryptosporidium paivum, Cyclospora cayetanenis, Toxoplasma gondii, Trichinella spiralis, Tanenia saginata, Taenia solium, Wuchereria bancrofti, Brugia malay, Brugia timori, Onchocerca vovulus, Loa loa, Dracunculus medinensis, Mansonella streptocera, Mansonella perstans, Mansonella ozzardi, Schistosoma hematobium, Schistosoma mansoni, Schistosoma japonicum, Ascaris lumbricoides, Entrobius vermicularis, Trichuris trichiura, Ancylostoma brasiliense, Ancylostoma duodenale, Necator ameicanus, Strongyloides stercoralis, Capillaria hepatica, Angiostrongylus cantonensis, Fasciola hepatica, Fasciola gigantica, Fasciolopsis buski, Chlonrchis sinensis, Heteropkves heterophyes, Paragonimus westermani, Diphyllobothrium latum, Hymenolepis nana, Hymenolepis dimunuta, Echinococcus granulosus, Dipylidium caninum, Entamoeba histolytica, Entamoeba coli, Entamoeba hartmanni, Dientamoeba fragilis, Endolimax nana, Lodomoeba butschilii, Blastocystis hominis, Giardia intetinalis, Chilomastix menili, Blantidium coli, Trichomonas vaginalis, Leishmania donovani, Tiypanosoma cruzi, Sarcocystis lindemanni*, and *Babesis argentina*. Fungal infections that can be treated by the methods of this aspect of the invention include, but are not limited to fungal meningitis, histoplasmosis, *Candida albicans* infection, as well as *Blastoimyces dermatitidis Histotplasma capsulatum, Cryptococcus neoformans, Sporothrix schenckii, Aspergillus fumigatus* and *Pneumocystis carinii* infections.

Angiogenesis-mediated disorders susceptible of treatment by the methods of the invention include solid and blood-borne tumors including but not limited to melanomas, carcinomas, sarcomas, rhabdomyosarcoma, retinoblastoma, Ewing sarcoma, neuroblastoma, osteosarcoma, and leukemia; diabetic retinopathy, rheumatoid arthritis, retinal neovascularization, choroidal neovascularization, macular degeneration, corneal neovascularization, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi's sarcoma, Mooren ulcer, Terrien's marginal degeneration, marginal keratolysis, traum, systemic lupus, polyarteritis, Wegeners sarcoidosis, scleritis, Steven's Jolmson disease, radial keratotomy, sickle cell anemia, sarcoidosis, pseudoxanthoma elasticum, Pagets disease, vein occlusion, artery occulsion, carotid obstructive disease, chronic uveitis, chronic vitritis, Lyme's disease, Eales disease, Bechets disease, myopia, optic pits, Stargarts disease, pars planitis, chronic retinal detachment, hyperviscosity syndromes, toxoplasmosis, post-laser complications, abnormal proliferation of fibrovascular tissue, hemangiomas, Osler-Weber-Rendu, acquired immune deficiency syndrome, ocular neovascular disease, osteoarthritis, chronic inflammation, Crohn's disease, ulceritive colitis, psoriasis, atherosclerosis, and pemphigoid. (See U.S. Pat. No. 5,712,291)

Bone disorders susceptible of treatment by the methods of the invention include but are not limited to bone fractures, defects, and disorders resulting in weakened bones such as ostepetrosis, osteoarthritis, rheumatoid arthritis, Paget's disease, osteohalisteresis, osteomalacia, periodontal disease, bone loss resulting from multiple myeloma and other forms of cancer, bone loss resulting from side effects of other medical treatment (such as steroids), age-related loss of bone mass and genetic diseases such as osteopetrosis. The polypeptides of the invention can be used alone or together with other compounds to treat bone disorders.

Immune suppressed illnesses or conditions susceptible of treatment by the methods of the invention include but are not limited to severe combined immune deficiency syndrome, acquired immune deficiency syndrome, and at risk populations including but not limited to malnourished individuals and senior citizens. Also susceptible of treatment are diseases such as cancer and viral infections, such as with HIV, in which the pathogenic agent or cell carries or produces an enzyme, N-acetyl-galactosaminidase, that removes GalNAc from Gc-MAF and thus destroys the activity of MAF. An effect of this enzymatic activity is a immuno-suppressed state that can be overcome by treatment with the polypeptides of the invention. Infectious agents may also cause destruction of important cells involved in modifying the precursor Gc protein to the active form Gc-MAF. For example, HIV causes loss of T-lymphocytes, which contain a sialidase that is involved in processing the precursor protein to its active form. Therefore, an immunosuppressed state can be caused by a decrease in processing the Gc-MAF precursor to the active protein and by further removal of the required sugar, which inactivates the protein. The polypeptides of the invention can be used alone or together with other compounds to treat immune suppressed illnesses.

The polypeptides of the invention can also be used as an analgesic to treat pain resulting from any cause, such as an underlying disease or trauma.

In a thirteenth aspect, the present invention provides methods for identifying a GalNAc-polypeptide mimetic, comprising:

a) contacting a plurality of test polypeptides with a GalNAc-binding protein, such as a lectin, under conditions to promote binding of the GalNAc binding protein with a polypeptide mimetic of GalNAc;

b) removing unbound test polypeptides;

c) repeating steps (a) and (b) a desired number of times;

d) contacting test polypeptides bound to the GalNAc-binding protein with an amount effective of free GalNAc to displace the bound test polypeptides if the bound test polypeptides are acting as GalNAc-mimetics; and e) identifying those test polypeptides that are displaced from the GalNAc binding protein by free GalNAc, wherein such test polypeptides are GalNAc-polypeptide mimetics.

In a preferred embodiment, the GalNAc binding proteins comprise lectins. Suitable GalNAc-specific lectins for use with the present invention are as described above.

As used herein the term "contacting" means in vivo or in vitro, preferably in vitro, under suitable conditions for promoting binding of the test polypeptides or compounds to GalNAc-specific lectin. Such techniques are known to those of skill in the art. The assays of the invention can be carried out, for example, as described in the Examples that follow. Modifications of these techniques are well within the level of those of skill in the art with respect to appropriate conditions for contacting as recited above that promote the appropriate binding, as well as techniques for removing unbound polypeptides and identifying the resulting GalNAc-polypeptide mimetics.

As recited in step (c), steps (a) and (b) can be carried out a desired number of additional times, which can be 0 repeats to as many as desirable, preferably between 1 and 5 repeats of step (a) and (b).

In a fourteenth aspect, the present invention provides methods for identifying a GalNAc mimetic compound, comprising:

a) contacting a plurality of test compounds with a GalNAc-specific lectin under conditions to promote binding of the GalNAc-specific lectin with a GalNAc mimetic compound;

b) removing unbound test compounds;

c) repeating steps (a) and (b) a desired number of times;

d) contacting test compounds bound to the GalNAc-binding protein with an amount effective of a polypeptide comprising or consisting of an amino acid sequence according to SEQ ID NOS:1-23, 29, 31-33, and 36-45 to displace the bound test compounds If the bound test compounds are acting as GalNAc-mimetics; and e) identifying those test compounds that are displaced from the GalNAc binding protein by a polypeptide comprising or consisting of an amino acid sequence according to SEQ ID NOS:1-23, 29, 31-33, and 36-45, wherein such test compounds are GalNAc mimetic compounds.

In a preferred embodiment, the GalNAc binding proteins comprise lectins. Suitable GalNAc-specific lectins for use with the present invention are as described above. Details of the methods of this fourteenth aspect are similar to those of the thirteenth aspect disclosed above. The test compounds can be, for example, polypeptides, small molecules, or nucleic acids. In a preferred embodiment, the test compounds are polypeptides.

In a further preferred embodiment of the thirteenth and fourteenth aspects, the methods further comprise synthesizing the GalNAc-polypeptide mimetics or test compound mimetics, using methods for synthesis known to those of skill in the art, and as disclosed herein.

In a further aspect, the present invention provides GalNAc mimetic polypeptides or compounds made according to the methods of the thirteenth and fourteenth aspects of the invention.

The test compounds (or test polypeptides) of the thirteenth and fourteenth aspects can, for example, be from compound libraries, expression libraries, and the like.

The present invention may be better understood with reference to the accompanying examples that are intended for purposes of illustration only and should not be construed to limit the scope of the invention, as defined by the claims appended hereto.

EXAMPLES

Because little more than the sugar and a few amino acids of DBP show phenotypic macrophage activation (Schneider et al., 2003), we designed a polypeptide structure that provides activation but which cannot be inactivated by deglycosylation. Amino acid sequences were identified that would mimic protein-bound GalNAc by screening a phage display library by first selecting phage particles that bind to GalNAc-specific lectins and subsequent elution with free GalNAc. An example of lectins that are useful in the screen is one purified from the snail *Helix pomatia*, which is highly specific for GalNAc (Hammerström and Kabat, 1971) and also binds specifically to the active form of Gc-MAF that contains GalNAc (Kanan et al., 2000). With the lectin as an analog of the receptor on macrophage cells, a polypeptide that binds to the lectin should mimic the structure of Gc-MAF.

The Ph.D.™-12 phage display polypeptide library (New England BioLabs, Inc.), which consists of randomized linear 12-mer polypeptides fused to protein pIII via the linker sequence GGGS (SEQ ID NO:34), was mixed with the *Helix pomatia* lectin conjugated to agarose beads (Sigma-Aldrich Co.). Phage particles that bound to the lectin were recovered by centrifugation, the complexes were washed and bound phage particles were released by a wash with 100 mM GalNAc. The phage were amplified and the 'panning' with the lectin-agarose conjugate was repeated two more times. Panning of the original library was also done with another Gal- NAc-specific lectin from *Vicia villosa* attached to agarose beads (Sigma-Aldrich Co.). Phage particles that bound to the lectin and were subsequently eluted by competition with free GalNAc were replicated, and the DNA of each was sequenced to derive the amino acid sequences of the variable region.

Table 1 shows amino acid sequences that were derived from the first round of the lectin screen. After three rounds of panning, sequence analysis of DNA of a set of selected phage particles indicated that the method allowed identification of a consensus amino acid sequence (VQATQSNQHTPR (Table 1, SEQ ID NO:3; see also FIG. 1). Although this consensus sequence appears to be optimal, flexibility exists in sequences that bind to the lectin, as indicated by the sequences shown in Table 1. The consensus sequence was used to synthesize polypeptides, either in single (linear) or multi-valent (branched) forms (FIG. 2). The "GGGS" sequence (see FIG. 1) is a spacer that is present in the mutagenized protein in all phage particles (i.e., not part of the variable region). This spacer was retained in some embodiments of the polypeptides of the present invention to move the mimetic sequence away from the C-terminal core of the branched structure, and kept the spacer in the linear sequence for consistency. The N-terminal "V" residue is preferred but not required.

TABLE 1

Amino acid sequences derived from DNA sequences of phage particles selected with GalNAc-specific lectins. Sequences are shown for the first round of panning with the *Helix pomatia* lectin.

| | | |
|---|---|---|
| 1. | AQALGLSAISPR | (SEQ ID NO: 1) |
| 2. | CTDEALYTRRQC | (SEQ ID NO: 2) |
| 3. | VQATQSNQHTPR | (SEQ ID NO: 3) |
| 4. | EQATPRNHHSPP | (SEQ ID NO: 4) |
| 5. | VQATPRLQHTPR | (SEQ ID NO: 5) |
| 6. | AQGPPSKQHSPP | (SEQ ID NO: 6) |
| 7. | LPTTINISNRGS | (SEQ ID NO: 7) |
| 8. | VPFRGYSPPQG | (SEQ ID NO: 8) |
| 9. | VQAIQSNQLTPR | (SEQ ID NO: 9) |
| 10. | VQATTVQIQHAP | (SEQ ID NO: 10) |
| 11. | CRASINITNRGS | (SEQ ID NO: 11) |
| 12. | LPSTINITNRGS | (SEQ ID NO: 12) |
| 13. | QSTTINIIRSGS | (SEQ ID NO: 13) |
| 14. | EEAISLISIRRR | (SEQ ID NO: 14) |
| 15. | VQAGQSNAHTAG | (SEQ ID NO: 15) |
| 16. | VQATQSNQHTPR | (SEQ ID NO: 3) |
| 17. | TTDEPFVYRRQP | (SEQ ID NO: 16) |
| 18. | VQARQSNQHTPR | (SEQ ID NO: 17) |
| 19. | VQANQCQSAYAR | (SEQ ID NO: 18) |
| 20. | VRLLQYAHRGRG | (SEQ ID NO: 19) |
| 21. | VQATQSNQHTPR | (SEQ ID NO: 3) |
| 22. | VQNYQSNQHTPR | (SEQ ID NO: 20) |
| 23. | FVSTTMKLSDG | (SEQ ID NO: 21) |
| 24. | FNSYDTEAFGGS | (SEQ ID NO: 22) |
| 25. | AETVESCLAK | (SEQ ID NO: 23) |

Multivalent structures were considered important because of the likelihood that activation requires cell-surface receptors to cluster. Glycopeptides containing multiple, closely-spaced clusters of GalNAc residues bind to a human macrophage C-type lectin with up to 38-fold greater affinity than a single GalNAc attached to the peptide (Iida et al., 1999). The data indicate that the preferred binding of glycopeptides is to the trimeric form of the human macrophage lectin (Iida et al., 1999). Polymers containing a cluster of GalNAc residues were found to be approximately $10^6$-fold more antigenic than a peptide containing a single sugar residue (Lo-Man et al., 1999). Thus clustering of the antigen is required for recognition by antibodies and the clusters are more active against macrophages than single Tn molecules. Branched polypeptide mimetics of this invention were synthesized with the multiple antigen polypeptide technology in light of these previous results.

These polypeptides showed a stimulatory activity in assays with blood cells that adhered to the surface of plastic microtiter plants, a characteristic of neutrophils and macrophages. Furthermore, infusion of the polypeptide into canine patients with several different cancers resulted in remarkable extension and improvement in the quality of life and in some cases a reduction in size of the primary tumor. No evidence was found for an immunogenic reaction against the polypeptide in the recipients after several months of treatment at the doses given, 10 to 200 mmoles per animal (dogs about 35 kg body weight). Thus, our chemical approach offers a major advance in the goal of achieving immunostimulant therapy.

Synthesis of the Mimetic

Figure 3:
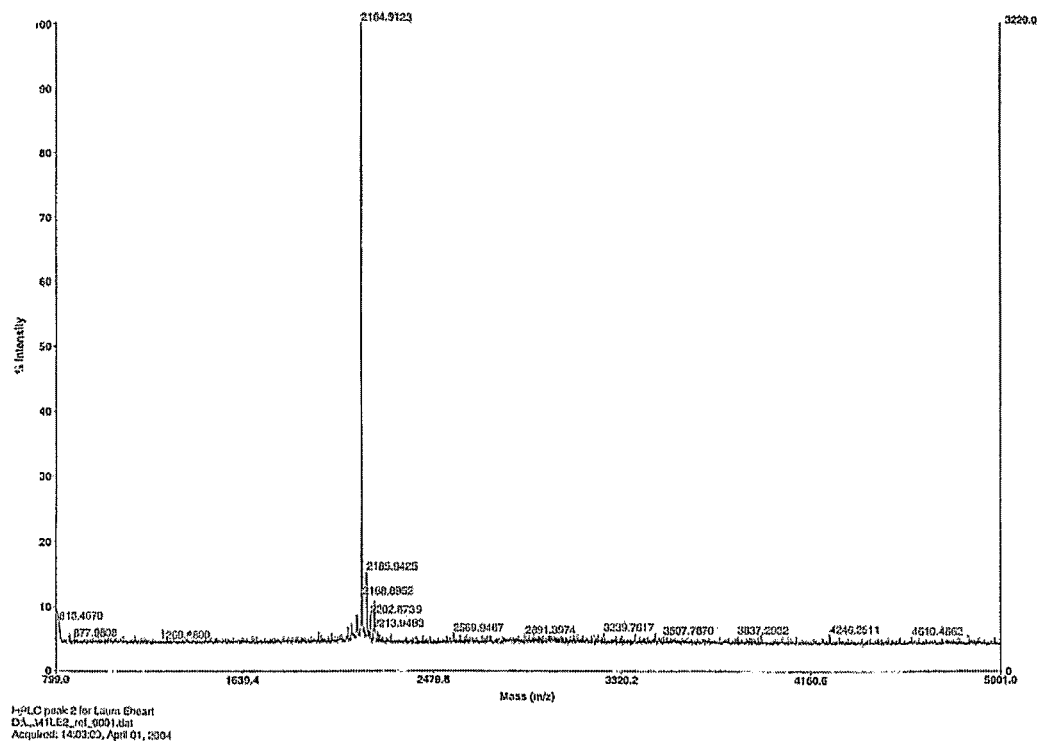
FIG. 3. Mass spectroscopic analysis of the linear peptide mimetic shown in FIG. 2. The analysis provided a molecular mass of 2,165 Daltons, which is the same as the predicted molecular mass of 2,165 Daltons.

The linear polypeptide mimetic (FIG. 2) was synthesized with standard methodology utilizing Fmoc (9-fluorenyl-methoxycarbonyl)-protected amino acids in a commercial continuous flow polypeptide synthesizer, with the sequence as VQATQSNQHTPRGGGSKW (SEQ ID NO:32). The polypeptide was synthesized with the C-terminal tryptophan (W) attached to the resin. The absorbance of tryptophan provides a means to measure concentration of the peptide. Biotin was incorporated into the polypeptide with ε-biotinyl-lysine as the penultimate C-terminal amino acid, in which biotin is attached through an amide linkage to the side-chain amino group of lysine. The biotin group, because of its high affinity with strepavidin, provides a means to retrieve the polypeptide with associated proteins from reaction mixtures to study interaction of the polypeptide with cellular components. Mass spectroscopy of the polypeptide product, purified by HPLC, detected a species with the correct predicted molecular weight (FIG. 3).

Figure 4:
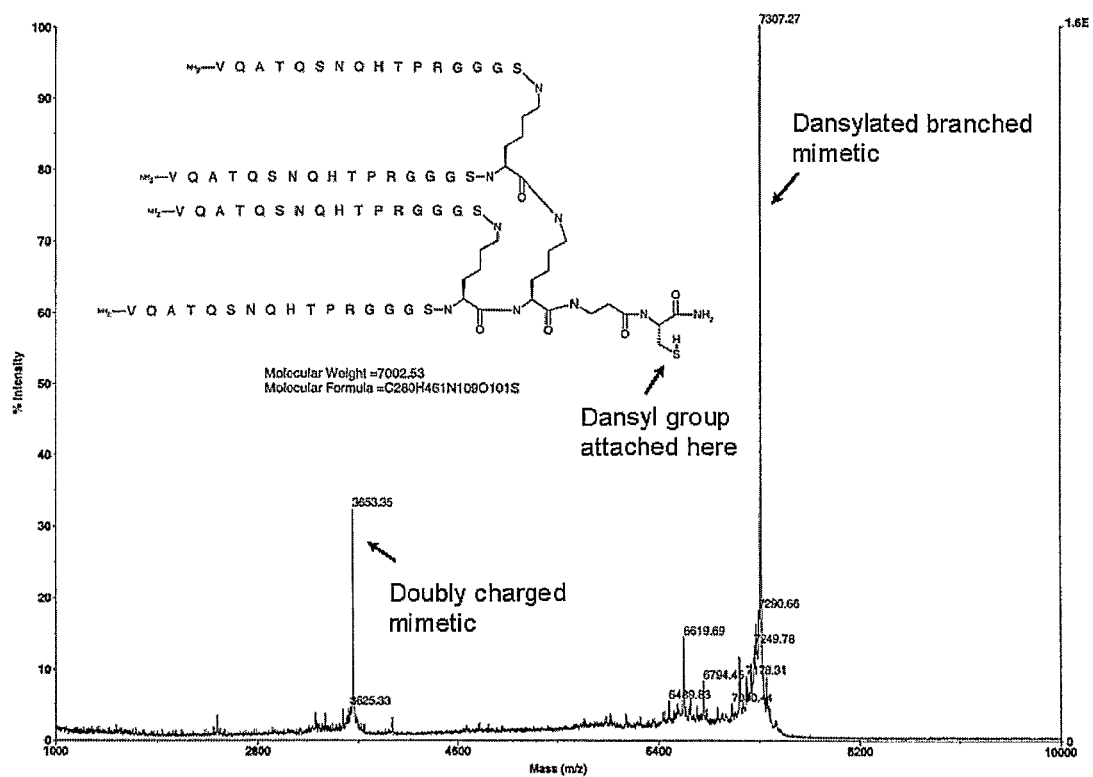
FIG. 4. Mass spectrometric analysis of the dansylated branched peptide mimetic structure shown in FIG. 2, with a calculated mass of 7,308 Daltons. The spectrum shows analysis of the mass (7,307.3 Daltons) of the purified peptide and the doubly charged peptide, 3,653 Daltons (mass/charge ratio). The structure of the undansylated peptide is shown in the figure.
Figure 5:
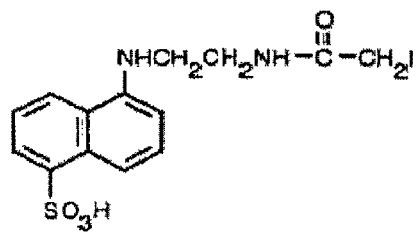
FIG. 5. Structure of the dansyl derivative attached to the peptide mimetic shown in FIG. 4. Addition occurs at the C-terminal cysteine residue by displacement of the iodine atom on the dansyl derivative by the sulfhydryl sulfur atom in the peptide.
Figure 7:
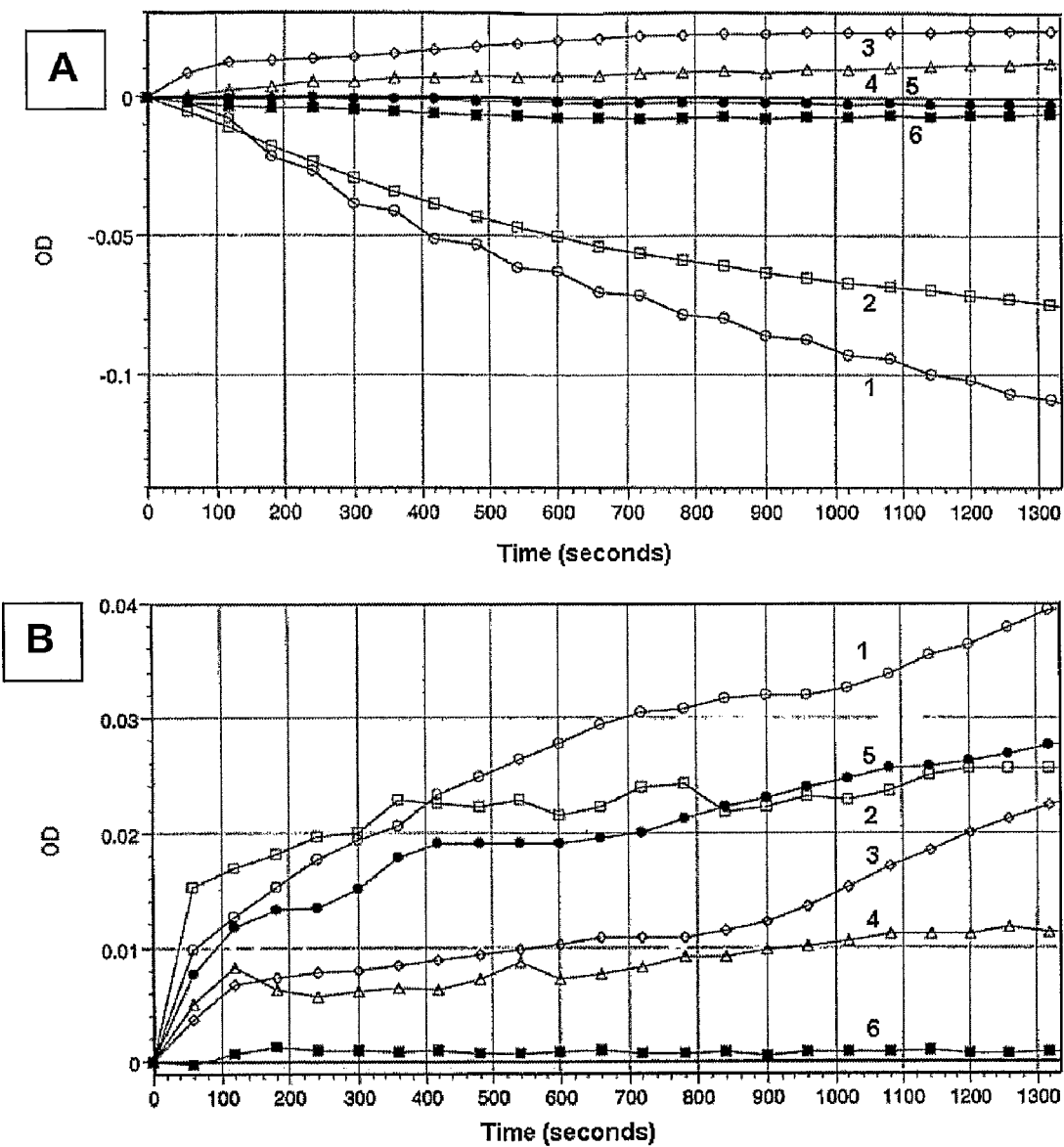
Figure 8:
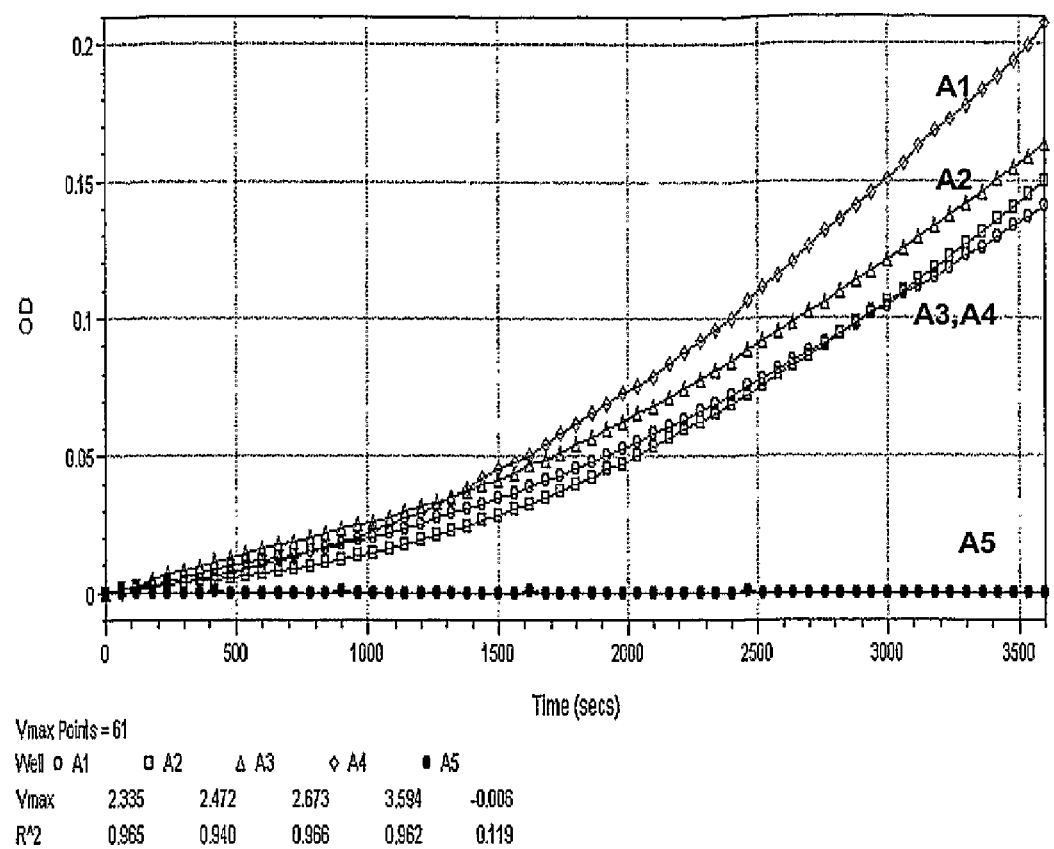
FIG. 8. Assay of pyrogallol oxidation initiated by superoxide anion radical generation by peripheral blood adherent cells treated with stimulants. Samples 1, 2, and 3, contained 3.4, 1.7 or 0.7 nM (25, 12.5 or 5 ng/ml) of the branched mimetic, respectively. Sample 4 contained 50 ng/ml lipopolysaccharide. Sample 5, untreated control cells.
Figure 9:
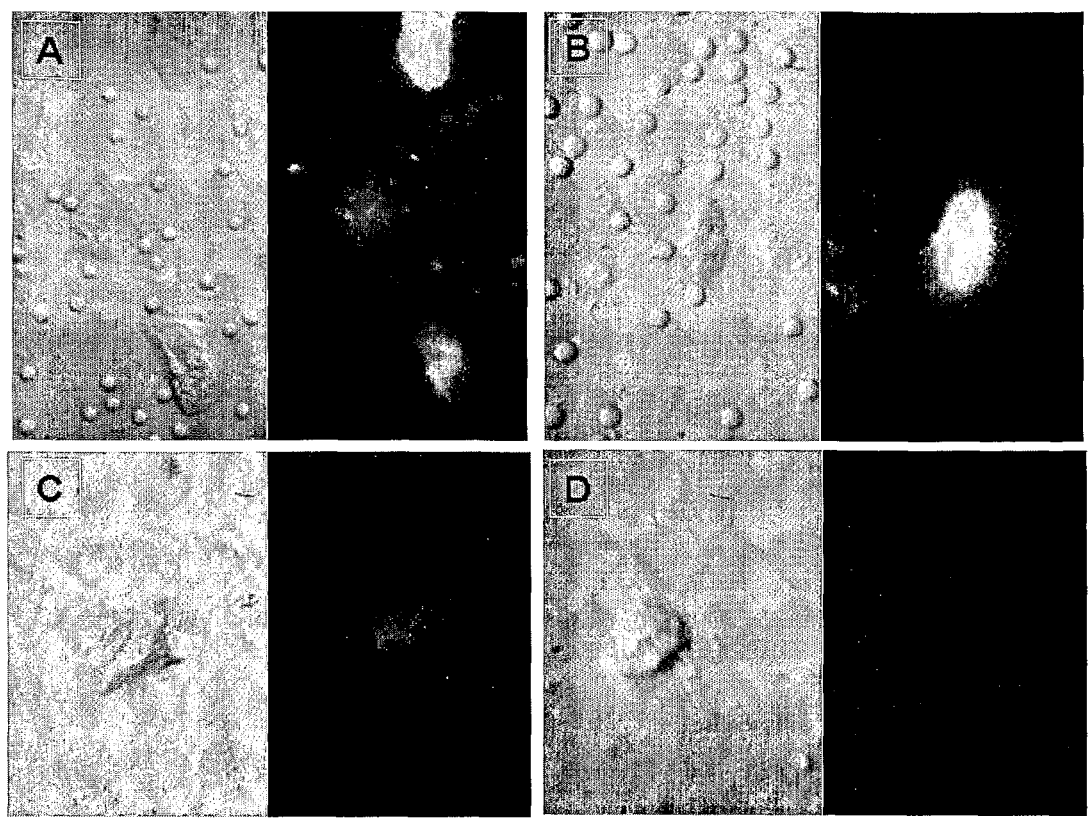
FIG. 9. Microscopic analysis of phagocytosis of fluorescently labeled bacterial cells by adherent cells from canine peripheral blood samples. Upper panels: (A), (B), In each pair, the right panel shows a fluorescent image of the light microscopic image shown in the left panel. The sample was treated 15 h with 5 nM branched peptide mimetic and then incubated with fluorescently-labeled bacterial cells for 10 min. Fluorescence of bacterial cells that remained extracellular was quenched with trypan blue. Lower panels: (C), (D), In each pair, the right panel shows a fluorescent image of the light microscopic image of cells in the left panel. The samples were not treated with the peptide mimetic, and most of the cells, as in (D) were not fluorescent. A very low level of fluorescence, evidence of low phagocytic activity, was occasionally seen, as shown in (C). Gain was set to maximize detection of fluorescence. Such control samples show the highest level of phagocytosis of bacterial that we have observed. In many experiments, control cells show no fluorescence.

The branched polypeptide (FIGS. 2 and 4) was synthesized, again by standard procedures with Fmoc-protected amino acids, in two stages. The C-terminal part of the polypeptide consisted of lysine(K)-βalanine(βA)-cysteine (C). Next, K was added to both the α- and ε-amino groups of K-βA-C to yield (K)$_2$K-βA-C, in which the α- and ε-amino groups of both terminal lysine residues are available for extension. The final product, therefore, is [(VQATQSNQHT- PRGGGS)$_2$K]$_2$KβAC (SEQ ID NO:33, see FIG. 2). A fluorophore was incorporated into this product by reaction with the thiol group on the C-terminal cysteine. The initial procedure involved dansylation using IAEDANS (Molecular Probes) (FIG. 5) following a standard Molecular Probes protocol for thiol-reactive probes. The product was purified by HPLC, and the purity is monitored by mass spectrometry (FIG. 4). The product was dried and then dissolved in sterile phosphate buffered saline, pH 7.4. Concentration was determined by absorbance of the fluorophore (extinction coefficient of this group, $\epsilon_{nM}$=5.7 cm$^{-1}$). A 1 mg/ml solution has an absorbance at 336 nm of 0.79. The product is stable for at least 3 months at 4° C. and longer when frozen.

Identification of an amino acid sequence that mimics the sugar GalNAc allows synthesis of a "glycoprotein" analog of Gc-MAF (SEQ ID NO:24-25) in systems that do not perform glycosylation of proteins. For example, high levels of protein expression can be achieved in bacteria and in the chloroplast of algae and plants, systems that do not have the capacity to synthesize most glycoproteins. We synthesized a gene for DomainIII of Gc-MAF (SEQ ID NO:26-27) with a nucleotide sequence that is optimized for codon usage in the bacterium *Escherichia coli* and in the chloroplast of the model alga *Chlamydomonas reinhardtii* (SEQ ID NOS:30-31). A chimeric human Domain III-polypeptide protein was also generated (SEQ ID NOS: 28-29) Similarities in codon usage in *E. coli* and the chloroplast of *Chlamydomonas* allow the same sequence to be expressed in both systems. Thus, SEQ ID NOS:30 and 31 are intended for expression of the same polypeptide in both organisms. Such constructs have the sugar mimetic placed within a larger carrier protein, which has the activity of Domain III that was expressed in the baculoviral system, one that is capable of glycosylation (Yamamoto and Naraparaju, 1997). The use of the mimetic to replace the sugar greatly simplifies the production of active Domain III or the full-length Gc-MAF in non-mammalian systems. Transformation of the chloroplast genome and the mechanism of expression of proteins within the chloroplast are similar to the processes in bacteria. *C. reinhardtii* chloroplasts are easily transformed by biolistic bombardment of cells with small gold beads that are covered with a vector DNA in which the gene of interest has been inserted. SEQ ID NO:31 shows the amino acid sequence of the product. The synthetic gene also encodes C-terminal poly-histidine to allow affinity purification.

Effect of Polypeptide Mimetic on Cellular Activity

Oxidative burst: Peripheral blood samples were removed from animals and 300 μl added to wells of a 96-well microtiter plate and incubated overnight at 38° C. in a standard $CO_2$-incubator. The nonadherent cells, including erythrocytes, and serum were removed and centrifuged to pellet cells and obtain cell-free serum. RPMI 1640 medium containing 2 to 10% serum from the same animal were added to each well and incubation of the culture is continued for various periods of time. The polypeptide mimetic was then added to a concentration of 1 to 10 nM and incubation continued for 3 h.

One type of assay of cellular activity measures the response of adherent cells to the polypeptide mimetic by the change in absorbance of cytochrome c (Johnston et al., 1978; Pick and Mizel, 1981). Phorbol 12-myristate 13-acetate (PMA) was added to 140 nM and then cytochrome c was added to 15 μM. Change in absorbance was monitored continuously at 550 nm over 20 min. With 300 μl in each well, reduction of cytochrome c was calculated as: Ananomoles=absorbance at 550 nm×100/2.1 (Pick and Mizel, 1981). Positive control samples were run with lipopolysaccharide, a known stimulator of macrophage activity. Negative controls lack stimulant. FIG. 7 shows results of representative, reproducible experiments.

The oxidative burst upon addition of PMA involves production of the superoxide anion radical. The superoxide anion radical is a strong reducing agent and reduces cytochrome c, which is detected by an increase in absorbance of the sample. Additionally, these cells produce the nitric oxide radical, which reacts with superoxide anion radical at diffusion-limited rates to produce the strong oxidant, peroxynitrite anion (Ischiropoulos et al., 1992). These strong oxidants apparently cause loss of absorbance of the cytochrome. In our assays, low concentrations of the mimetic polypeptide (1 nM) or lipopolysaccharide resulted typically in an increase in absorbance of cytochrome c. Higher concentrations of polypeptide (5 to 10 μM) consistently caused rapid loss of absorbance, evidence of destruction of cytochrome c (FIG. 7A).

FIG. 7B shows an experiment in which the number of cells was lowered to allow cytochrome c to compete effectively for the reactive superoxide anion when less nitric oxide was produced. Without treatment with the polypeptide, again no change in absorbance of the cytochrome was detected. The rate of reduction of cytochrome c correlated with the amount of polypeptide mimetic added. These results are typical of those in the literature with activated macrophages, which were commonly reported as single-point measurements at 10 or 20 min rather than time courses shown in FIG. 7. The branched polypeptide mimetic caused a stronger response than the linear polypeptide. These results show a strong response by the cells to the branched polypeptide, even stronger than to lipopolysaccharide, on an equal weight basis, in stimulating the oxidative burst.

The response of cells to the polypeptide was also assayed by oxidation of pyrogallol (Marklund and Marklund, 1974) in a reaction initiated by superoxide anion radical (FIG. 8). The polypeptide mimetic was the most active stimulant in these experiments, which confirmed activity of the polypeptide on cells by biochemical assays in vitro.

Phagocytosis: Phagocytosis was measured by the uptake of fluorescently-labeled bacterial cells (Molecular Probes, Inc.) or fluorescent polystyrene beads (Polyscience, Inc). Phagocytosis can be quantitated by quenching extracellular (unphagocytized) bacterial cells by addition of the dye trypan blue to the suspension and measuring the remaining (intracellular) fluorescence (Wan et al., 1993).

In one experiment, canine peripheral blood macrophages were treated for 15 hours with 5 nM branched polypeptide (SEQ ID NO:33), and then incubated with bacterial cells for 10 minutes, followed by microscopic analysis. Fluorescence of bacterial cells that remained extracellular was quenched with trypan blue. These experiments showed that treatment of the cells with the branched polypeptide dramatically increased phagocytosis of the bacterial cells by the peripheral blood macrophages. (See FIG. 9)

In another experiment, adherent canine peripheral blood cells were treated for 5 hours with 10 nM branched polypeptide (SEQ ID NO:33) and then washed. Fluorescent bacterial cells were added, and after 10 minutes, trypan blue was added to quench extracellular bacterial cells. Cells were examined by light microscopy and then by fluorescent microscopy. Contrast in the fluorescent images was maximized to detect any fluorescence in control samples. The images also show that more of the smaller neutrophils become attached in the treated samples, although they do not become fluorescent. Treated and control samples were from the same dog. These experiments showed that treatment of the cells with the polypeptide dramatically increased phagocytosis of the bacterial cells by the peripheral blood macrophages.

Phagocytosis of polystyrene beads: Peripheral blood from the canines was added to confocal dishes and incubated over night to allow macrophage adherence. The cells were washed away with PBS, HBSS, or RPMI. Only adherent macrophages or neutrophils remained on the glass surface and were left to incubate in the above mentioned buffers. Polypeptide was then added at 3.4 nM (25 ng/ml) for a 5-hour incubation. At this point, beads were added for a 10-minute incubation. All incubations were done in 37° C. with 5% $CO_2$. Within 10 to 30 minutes after addition, microscopic examination showed the presence of the beads within cells. Unstimulated cells exhibited a low level of phagocytosis or did not contain any detectable fluorescent beads inside the cells. In addition, the polypeptide mimetic induced detachment of neutrophils from the surface, an indication of the chemotaxis that is primed by the vitamin D-binding protein (Binder et al., 1999).

These assays of phagocytic activity induced by the polypeptides of the invention allow correlation of activity at the cellular level during the course of treatment of each animal.

Pharmacokinetic Analysis

The polypeptide was tagged with a fluorescent dansyl group to follow the life-time of the polypeptide in blood. Preliminary analyses have shown that a portion of the polypeptide, approximately two-thirds, binds to proteins when added to serum. The association of the polypeptide with proteins may be advantageous to prevent rapid removal from the circulatory system as the result of clearance of small proteins by the kidneys (Goochee et al., 1991). The sensitivity of the fluorescence measurements allows analysis of the polypeptide concentration to levels 100-fold less than the initial level. This range is sufficient to determine half-life of the polypeptide in vivo.

Pre-Clinical Observations

Owners of dogs that were used to obtain preliminary data were required to sign informed consent and agreement to necropsy forms. Dogs with histologically or cytologically confirmed cancer were given the polypeptide mimetic at doses of 100 to 1,500 μg by weekly perfusion into the blood or subcutaneously 3 times per week. The effective dose of the glycopeptide used by Schneider et al. (2003) was 0.4 ng/g body weight given every other day. On this basis, a minimal weekly dose should be 1.4 ng/g body weight. For a large animal (80 lb or 36 kg dog), the starting, minimal-effective, weekly dose of the synthetic mimetic polypeptide would therefore be 50 μg or 6.8 nmoles. For initial studies, the mimetic polypeptide (SEQ ID NO:33) was administered at a 20-fold higher dose. Canine patients with spontaneous malignancies, all of which had been treated with chemotherapy but had recurring, advanced cancer at the initiation of treatment, were treated with the branched polypeptide mimetic. No adverse side effects were noted by a veterinarian oncology specialist, with several animals surviving 6 months or more on the treatment. Subjectively, quality of life was dramatically enhanced with the use of the polypeptide mimetic and several patients appeared to have extension of life beyond what would be normally expected with their advanced cancer. With several patients, behavior was restored to pre-disease activities and a reduction in tumor load was detected. Although the treatment seems to hold great promise, data are limited because of the short period of treatment and small population size.

REFERENCES

U.S. Pat. No. 6,410,269
U.S. Patent Application Publication 20030229014
U.S. Patent Application Publication 20040058859
Babino, A., Tello, D., Rojas, A., Bay, S., Osinaga, E. and Alzari, P. M. (2003) The crystal structure of a plant lectin in complex with the Tn antigen. FEBS Lett. 536, 106-110.
Binder, R., Kress, A., Kan, G., Herrmann, K. and Kirschfink, M. (1999) Neutrophil priming by cytokines and vitamin D binding protein (Gc-globulin): impact on C5a-mediated chemotaxis, degranulation and respiratory burst. Molec. Immunol. 36, 885-892.
Cooke, N. E. and David, E. V. (1985) Serum vitamin D-binding protein is a third member of the albumin and alpha fetoprotein gene family. J. Clin. Invest. 76, 2420-2424.
Coppenhaver, D. H., Sollenne, N. P. and Bowman, B. H. (1983) Post-translational heterogeneity of the human vitamin D-binding protein (group-specific component). Arch. Biochem. Biophys. 226, 218-223.
Gomme, P. T. and Bertolini, J. (2004) Therapeutic potential of vitamin D-binding protein. Trends Biotechnol. 22, 340-345.
Goochee, C. F., Gramer, M. J., Andersen, D. C., Bahr, J. B. and Rasmussen, J. R. (1991) The oligosaccharides of glycoproteins: bioprocess factors affecting oligosaccharide structures and their effect on glycoprotein properties. Bio/Technology 9, 1347-1355.
Hammarström. S, and Kabat, E. A. (1971) Studies on specificity and binding properties of the blood group A reactive hemagglutinin from *Helix pomatia*. Biochemistry 10, 1684-1692.
Head, J. F., Swamy, N and Ray, R. (2002) Crystal structure of the complex between actin and human vitamin D-binding protein at 2.5A resolution. Biochemistry 41, 9015-9020.
Iida, S., Yamamoto, K. and Irimura, T. (1999) Interaction of human macrophage C-type lectin with O-linked N-acetylgalactosamine residues on mucin glycopeptides. J. Biol. Chem. 274, 10697-10705.
Ischiropoulos, H., Zhu, L and Beckman, J. S. (1992) Peroxynitrite formation from macrophage-derived nitric oxide. Arch. Biochem. Biophys. 298, 446-451.
Johnston, R. B., Godzik, C. A. and Cohn, Z. A. (1978) Increased superoxide anion produced by immunologically activated and chemically elicited macrophages. J. Exp. Med. 148, 115-126.
Kanan, R. M., Cook, D. B. and Dafta, H. K. (2000) Lectin immunoassay for macrophage activating factor (Gc-MAF) produced by deglycosylation of Gc-globulin: evidence for noninducible generation of Gc-MAF. Clin. Chem., 46, 412-414.
Kanda S., Mochizulci, Y., Miyata, Y., Kanetake, H. and Yamamoto, N. (2002) Effects of vitamin $D_3$-binding protein-derived macrophage activating factor (GcMAF) on angiogenesis. J. Natl. Cancer Inst. 94, 1311-1319.
Kisker, O., Onizuka, S., Becker, C. M., Fannon, M., Flynn, E., D'Amato, R., Zefter, B., Folknman, J., Ray, R., Swamy, N., and Pirie-Sheperd, S. (2003) Vitamin D binding protein-macrophage activating factor (DBP-maf) inhibits angiogenesis and tumor growth in mice. Neoplasia 5, 32-40.
Kolatkar, A. R., Leung, A. K., Isecke, R., Brossmer, R., Drickamer, K. and Weis, W. L. (1998) Mechanism of N-acetylgalactosamine binding to a C-type animal lectin carbohydrate-recognition domain. J. Biol. Chem. 273, 19502-19508.
Lo-Man, R., Bay, S., Vichier-Guerre, S., Dériaud, E., Cantacuzène, D. and Leclerc, C. (1999) A fully synthetic immunogen carrying a carcinoma-associated carbohydrate for active specific immunotherapy. Cancer Res. 59, 1520-1524.

Lo-Man, R., Vichier-Guerre, S., Bay, S., Dériaud, E., Cantacuzeme, D. and Leclerc, C. (2001) Anti-tumor immunity provided by a synthetic multiple antigenic glycopeptide displaying a tri-Tn glycotope. J. Immunol. 166, 2849-2854.

Lo-Man, R., Vichier-Guerre, S., Perraut, R., Dériaud, E., Huteau, V., BenMohamed, L., Diop, O. M., Livingston, P. O., Bay, S, and Leclerc, C. (2004) A fully synthetic therapeutic vaccine candidate targeting carcinoma-associated Tn carbohydrate antigen induces tumor-specific antibodies in nonhuman primates. Cancer Res. 64, 4987-4994.

Loris, R., Hamelryck, T, Bouckaert, J. and Wyns, L. (1998) Legume lectin structure. Biochim. Biophys. Acta 1383, 9-36.

Marklund, S, and Marklund, G. (1974) Involvement of superoxide anion radical in the auto-oxidation of pyrogallol and a convenient assay of superoxide dismutase. Eur. J. Biochem. 47, 469-474.

Onizuka, S., Kawakami, S., Taniguchi, K, Fujioka, H. and Miyashita, K. (2004) Pancreatic carcinogenesis: apoptosis and angiogenesis. Pancreas 28, 317-319.

Osinaga, E., Tello, D., Batthyany, C., Bianchet, M., Tavares, G., Duràn, R., Cerveñansky, C., Camoin, L., Roseto, A. and Alzari, P. M. (1997) Amino acid sequences and three-dimensional structure of the Tn-specific isolectin B4 from *Vicia villosa*. FEBS Lett. 412, 190-196.

Otterbein, L. R., Cosio, C., Graceffa, P. and Dominguez, R. (2002) Crystal structure of the vitamin D-binding protein and its complex with actin: structural basis of the actin-scavenger system. Proc. Natl. Acad. Sci. USA 99, 8003-8008.

Pick, E. and Mizel, D. (1981) Rapid microassays for the measurement of superoxide and hydrogen peroxide production by macrophages in culture using an automatic enzyme immunoassay reader. J. Immunol. Meth. 46, 211-226.

Rabijns, A., Verboven, C., Rougè, P., Barre, A., Van Damme, E. J. M., Peumans, W. J., De Ranter, C. J. (2001) Structure of a legume lectin from the bark of *Robinia pseudoacacia* and its complex with N-acetylgalactosamine. Proteins 44, 470-478.

Schneider, G., Benis, K., Flay, N., Ireland, R. and Popoff, S. (1995) Effects of vitamin D-binding protein-macrophage activating factor (DBP-MAF) infusion on bone resorption in two osteopetrotic mutations. Bone 16, 657-662.

Schneider, G. B., Grecco, K. J., Safadi, F. F. and Popoff, S. N. (2003) The anabolic effects of vitamin D-binding protein-macrophage activating factor (DBP-MAF) and a novel small polypeptide on bone. Critical Rev. Eukaryotic Gene Exp. 13, 277-284.

Sugawara, H., Kusunoki, M., Kurisu, G., Fujimoto, T., Aoyagi, H. and Hatakeyama, T. (2004) Characteristic recognition of N-acetylgalactosamine by an invertebrate C-type lectin, CEL-I, revealed by X-ray crystallographic analysis. J. Biol. Chem. 279, 45219-45225.

Verboven, C., Rabijns, A., De Maeyer, M., Van Baeten, H., Bouillon, R. and De Ranter, C. (2002) A structural basis for the unique binding features of the human vitamin D-binding protein. Nature Struct. Biol. 9, 131-136.

Viau, M., Constans, H., Debray, H. and Montreuil, J. (1983) Isolation and characterization of the o-glycan chain of the human vitamin D-binding protein. Biochem. Biophys. Res. Commun. 117, 324-331.

Vichier-Guerre, S., Lo-Man, R., Bay, S., Deriaud, E., Nakada, H, Leclerc, C. and Cantacuzéne, D. (2000) Short synthetic glycopeptides successfully induce antibody responses to carcinoma-associated Tn antigen. J. Peptide Res. 55, 173-180.

Wan, C. P., Park, C. S, and Lau, B. H. S. (1993) A rapid and simple microfluorometric phagocytosis assay. J. Immunol. Meth. 162, 1-7.

White, P. and Cooke, N. (2000) The multifunctional properties and characteristics of vitamin D-binding protein. Trends Endocrin. Metabol. 11, 320-327.

Yamamoto, N. and Homma, S. (1991) Vitamin $D_3$ binding protein (group-specific component) is a precursor for the macrophage-activating signal factor from lysophosphatidylcholine-treated lymphocytes. Proc. Natl. Acad. Sci. USA 88, 8539-8543.

Yamamoto, N. and Kumashiro, R. (1993) Conversion of vitamin $D_3$-binding protein (group-specific component) to a macrophage-activating factor by the stepwise action of β-galactosidase of B cells and sialidase of T cells. J. Immunol. 151, 2794-2802.

Yamamoto, N. and Naraparaju V. R. (1996a) Vitamin $D_3$-binding protein as a precursor for macrophage activating factor in the inflammation-primed macrophage activation cascade in rats. Cell. Immunol. 170, 161-167.

Yamamoto, N. and Naraparaju, V. R. (1996b) Role of vitamin $D_3$-binding protein in activation of mouse macrophages. J. Immunol. 157, 1744-1749.

Yamamoto, N. and Naraparaju, V. R. (1997) Immunotherapy of BALB/c mice bearing Ehrlich ascites tumor with vitamin C-binding protein-derived macrophage activating factor. Cancer Res. 57, 2187-2193.

Yamamoto, N. and Naraparaju, V. R. (1998) Structurally well-defined macrophage activating factor derived from vitamin $D_3$-binding protein has a potent adjuvant activity for immunization. Immunol. Cell Biol. 76, 237-244.

Yamamoto, N., Naraparaju, V. R. and Asbell, S. O. (1996) Deglycosylation of serum vitamin $D_3$-binding protein leads to immunosuppression in cancer patients. Cancer Res. 56, 2827-2831.

Yamamoto, N., Naraparaju, V. and Orchard, P. J. (1996) Defective lymphocyte glycosidases in the macrophage activation cascade of juvenile osteopetrosis. Blood 88, 1473-1478.

Yamamoto, N., Naraparaju, V. R and Srinivasula, S. M. (1995) Structural modification of serum vitamin $D_3$-binding protein and immunosuppression in AIDS patients. AIDS Res. Human Retrovir. 11, 1373-1378.

Yamamoto, N., Naraparaju, V. R and Urade, M. (1997) Prognostic utility of serum α-N-acetylgalactosamindase and immunosuppression resulted from deglycosylation of serum Gc protein in oral cancer patients. Cancer Res. 57, 295-299.

Yang, F., Bergeron, J. M., Linehan, L. A., Lalley, P. A., Sakaguchi, A. L. and Bowman, B. H. (1990) Mapping and conservation of the group-specific component gene in mouse. Genomics 7, 509-516.

Yang, F., Brune, J. L., Maylor, S. L., Cupples, R. L., Naberhaus, K. H. and Bowman, B. H. (1985) Human group-specific component (Gc) is a member of the albumin family. Proc. Natl. Acad. Sci. USA 82, 7994-7998.

We claim:

1. A substantially purified polypeptide consisting of an amino acid sequence according to formula 1:

B1-[X1-Q-X2-X3-X4-X5-X6-X7-X8-X9-X10-X11]-B2;

wherein X1 is selected from the group consisting of V, E, and A, or is absent;
X2 is selected from the group consisting of A, N, and G;
X3 is any amino acid;
X4 is selected from the group consisting of P and Q;
X5 is selected from the group consisting of S, R, and C;
X6 is selected from the group consisting of N, L, G, and K;
X7 is selected from the group consisting of Q, A, S, and H;
X8 is selected from the group consisting of H, L, and A;
X9 is selected from the group consisting of S and T;
X10 is selected from the group consisting of P and A;
X11 is selected from the group consisting of R, G, and P; and
wherein B1 and B2 are independently 1-5 amino acids, or are absent.

2. The substantially purified polypeptide of claim 1, wherein
X1 is V or is absent;
X2 is selected from the group consisting of A and N
X5 is selected from the group consisting of S and R;
X6 is N;
X7 is selected from the group consisting of Q and A;
X8 is selected from the group consisting of H and L; and
X11 is selected from the group consisting of R and G.

3. The substantially purified polypeptide of claim 1, wherein
X1 is V or is absent;
X2 is A;
X3 is any amino acid;
X4 is Q;
X5 is S;

X6 is N;
X7 is Q;
X8 is H;
X9 is T;
X10 is P; and
X11 is R.

4. The substantially purified polypeptide of claim 3 wherein X3 is T.

5. A peptide comprising multiple copies of the substantially purified polypeptide of claim 1.

6. The peptide of claim 5 where the peptide is branched.

7. A pharmaceutical composition comprising the substantially purified polypeptide of claim 1 and a pharmaceutically acceptable carrier.

8. A substantially purified nucleic acid composition comprising a nucleic acid sequence that encodes a polypeptide according to claim 1.

9. A recombinant expression vector comprising the substantially purified nucleic acid sequence of claim 8.

10. A recombinant host cell transfected with the recombinant expression vector of claim 9.

11. A method for stimulating immune system activity in a subject, comprising administering to a subject an amount effective of a polypeptide according to claim 1 thereby stimulating immune system activity.

12. The method of claim 11 wherein the subject is suffering from an infection.

13. The method of claim 11 wherein the subject has a tumor.

14. The method of claim 11 wherein the subject has a bone disorder.

15. The method of claim 11 wherein the subject is in need of anti-angiogenic therapy.

16. The method of claim 11 wherein the subject is suffering from an immune suppressed disorder.

17. The method of claim 11 wherein the subject is suffering from pain.

18. The method of claim 11 wherein the subject is also receiving a vaccination.

19. An improved method of vaccination in a subject, comprising administering to a subject receiving a vaccination an effective amount of a polypeptide according to claim 1 for promoting an improved immune system response to the vaccination.

20. A substantially purified polypeptide consisting of an amino acid sequence selected from the group consisting of SEQ ID NOs: 3-6, 9, 15, 17, 20, 32, 36, 37, 40, 41 and 44.

* * * * *